(12) United States Patent
Mazzocchi et al.

(10) Patent No.: US 11,571,288 B2
(45) Date of Patent: Feb. 7, 2023

(54) URETHRAL ARTIFICIAL SPHINCTER WITH BISTABLE ACTUATION SYSTEM

(71) Applicants: SCUOLA SUPERIORE DI STUDI UNIVERSITARI E DI PERFEZIONAMENTO SANT'ANNA, Pisa (IT); INAIL—ISTITUTO NAZIONALE PER L'ASSICURAZIONE CONTRO GLI INFORTUNI SUL LAVORO, Rome (IT)

(72) Inventors: Tommaso Mazzocchi, Montecatini Terme (IT); Arianna Menciassi, Pontedera (IT); Leonardo Ricotti, Peccioli (IT); Gioia Lucarini, Marina di Pietrasanta (IT); Leonardo Marziale, Pisa (IT); Rinaldo Sacchetti, Novafeltria (IT)

(73) Assignees: SCUOLA SUPERIORE DI STUDI UNIVERSITARI E DI PERFEZIONAMENTO SANT'ANNA, Pisa (IT); INAIL—ISTITUTO NAZIONALE PER L'ASSICURAZIONE CONTRO GLI INFORTUNI SUL LAVORO, Rome (IT)

( * ) Notice: Subject to any disclaimer, the term of this patent is extended or adjusted under 35 U.S.C. 154(b) by 363 days.

(21) Appl. No.: 16/767,563

(22) PCT Filed: Nov. 28, 2018

(86) PCT No.: PCT/IB2018/059432
§ 371 (c)(1),
(2) Date: May 27, 2020

(87) PCT Pub. No.: WO2019/106581
PCT Pub. Date: Jun. 6, 2019

(65) Prior Publication Data
US 2020/0383764 A1  Dec. 10, 2020

(30) Foreign Application Priority Data
Nov. 28, 2017  (IT) .................. 102017000136714

(51) Int. Cl.
*A61F 2/00* (2006.01)

(52) U.S. Cl.
CPC .......... *A61F 2/0018* (2013.01); *A61F 2/0004* (2013.01); *A61F 2/0022* (2013.01);
(Continued)

(58) Field of Classification Search
None
See application file for complete search history.

(56) References Cited

U.S. PATENT DOCUMENTS

| | | | |
|---|---|---|---|
| 3,731,670 A | 5/1973 | Loe | |
| 6,409,656 B1 * | 6/2002 | Sangouard | ............ A61F 2/0018 600/30 |
| 2007/0276342 A1 | 11/2007 | Lin et al. | |

FOREIGN PATENT DOCUMENTS

| | | |
|---|---|---|
| CN | 2307961 Y | 2/1999 |
| DE | 102012200156 A1 | 7/2013 |

(Continued)

OTHER PUBLICATIONS

Grunemberger, A.D., et al. "A magnet system for urethral closure in females," Journal Biomedical Engineering, vol. 6, No. 2, pp. 102-106 (Apr. 1984).

*Primary Examiner* — Suba Ganesan
(74) *Attorney, Agent, or Firm* — Maschoff Brennan

(57) ABSTRACT

An artificial sphincter to be implanted in a urethra, for treating patients suffering from urinary incontinence, includes a container configured to be connected to a wall of a urethra, inside or outside it, a valve unit housed within the container and configured to move from a release configuration to a block configuration and vice-versa. An actuation magnet is movably (rotatably or slidably) arranged between a first and a second position in the container, and is connected to the valve unit such that a predetermined (rotation or translation) movement of the actuation magnet from a first towards a second position, or from the second towards the first position, under the effect of an external manoeuvre magnet, brings the valve unit from the release configuration to the block configuration, where the valve is stably main- (Continued)

tained, and from the block configuration to the release configuration, where the valve is stably maintained.

8 Claims, 19 Drawing Sheets

(52) U.S. Cl.
CPC ...... *A61F 2/0036* (2013.01); *A61F 2210/009* (2013.01); *A61F 2250/0001* (2013.01)

(56) References Cited

FOREIGN PATENT DOCUMENTS

| | | |
|---|---|---|
| JP | 2006025818 A | 2/2002 |
| WO | 2004/037134 A1 | 5/2004 |
| WO | 2012/120326 A1 | 9/2012 |
| WO | 2013/144770 A1 | 10/2013 |
| WO | 2014/205271 A1 | 12/2014 |

* cited by examiner

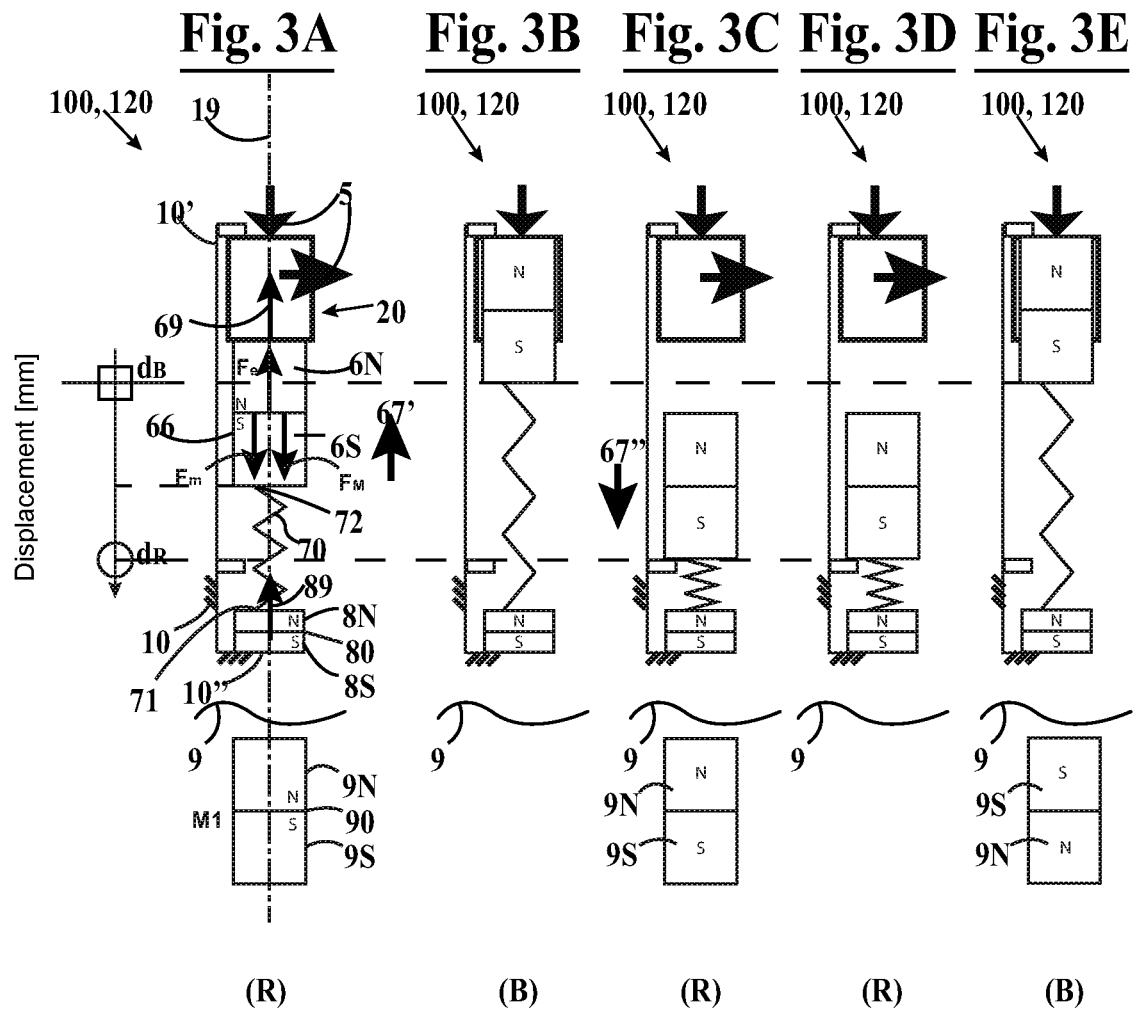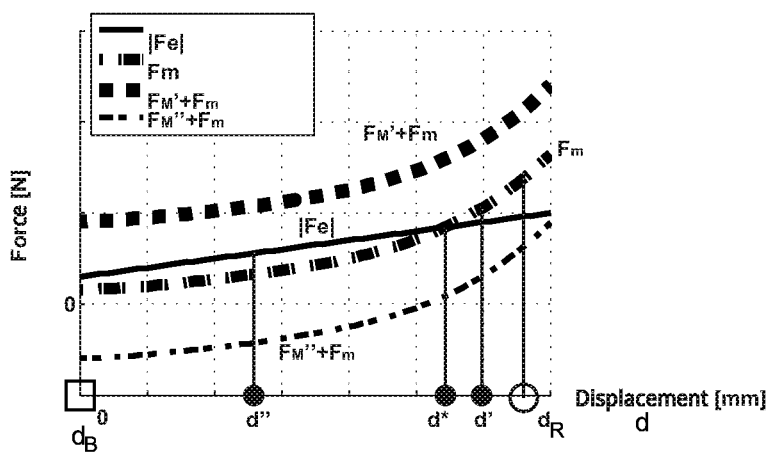

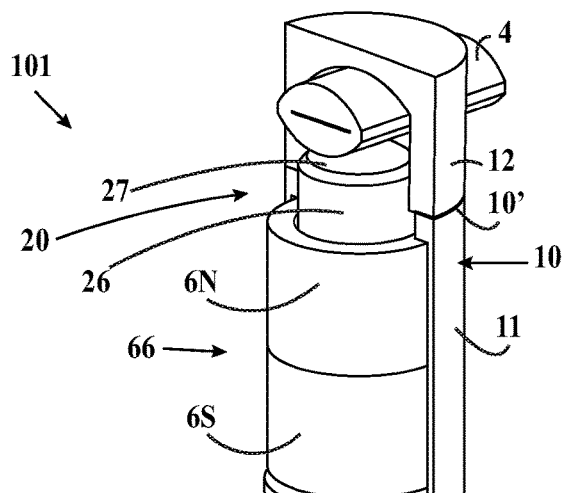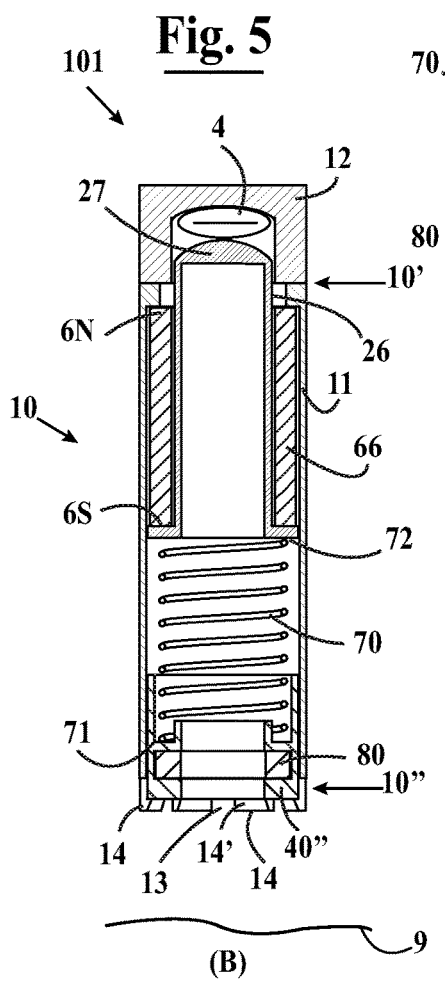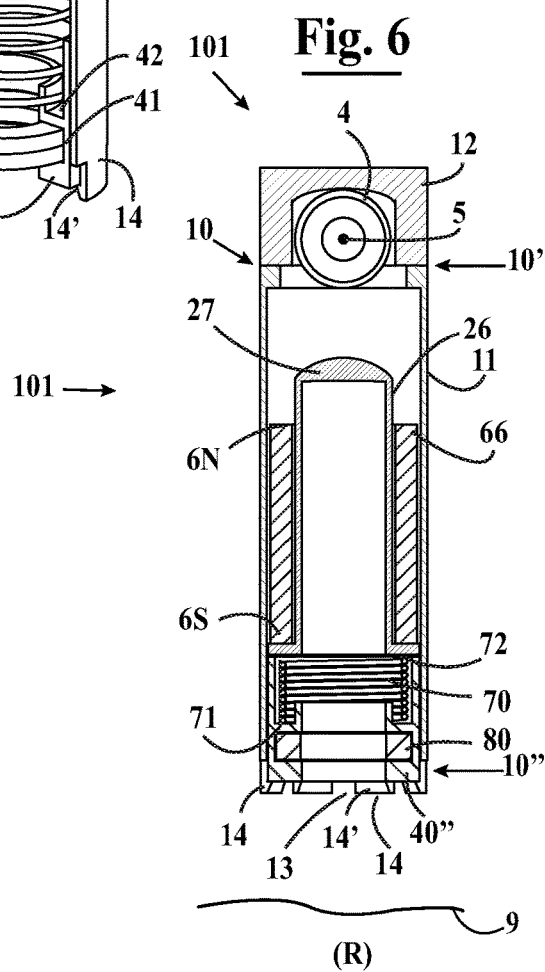

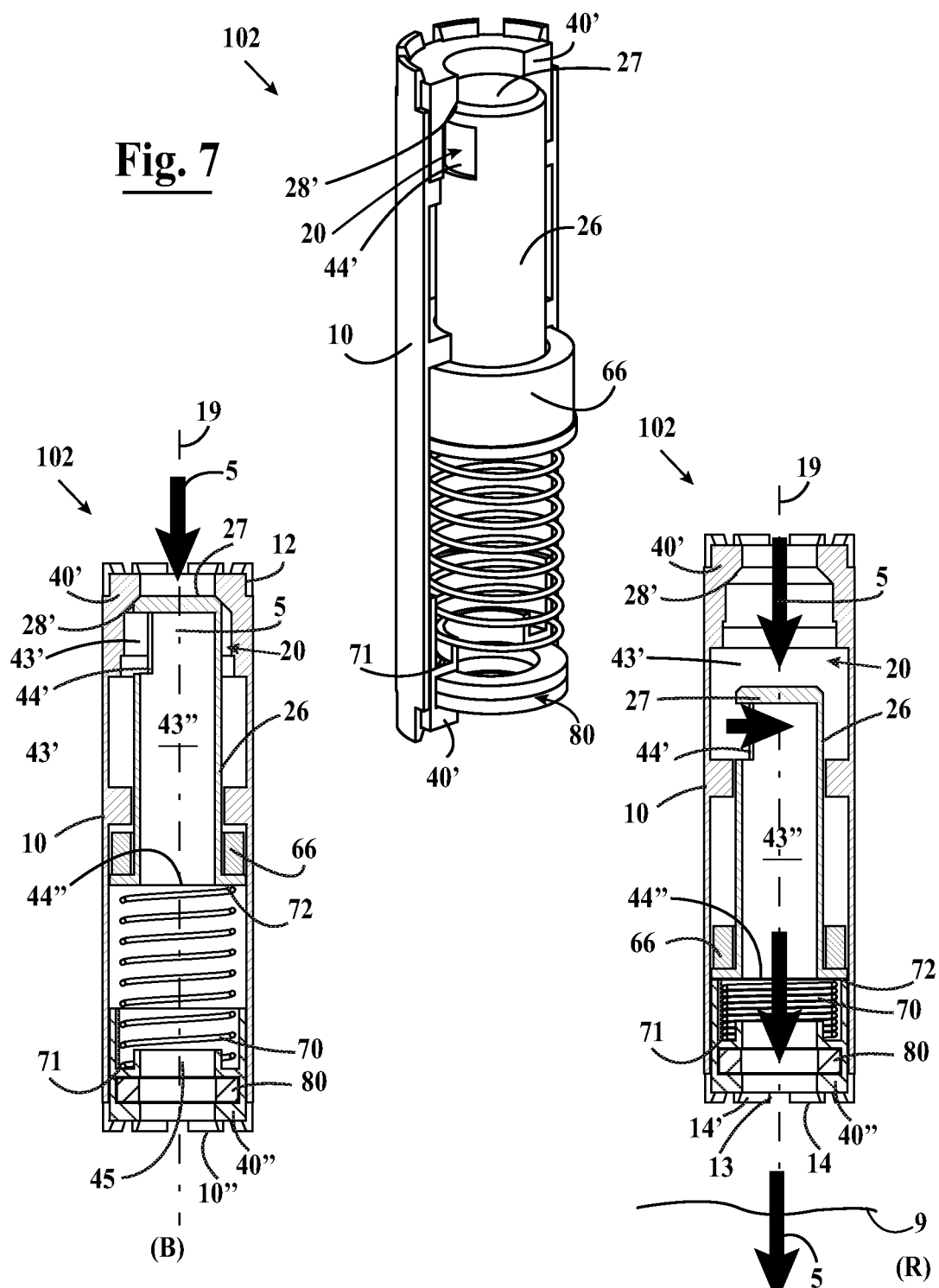

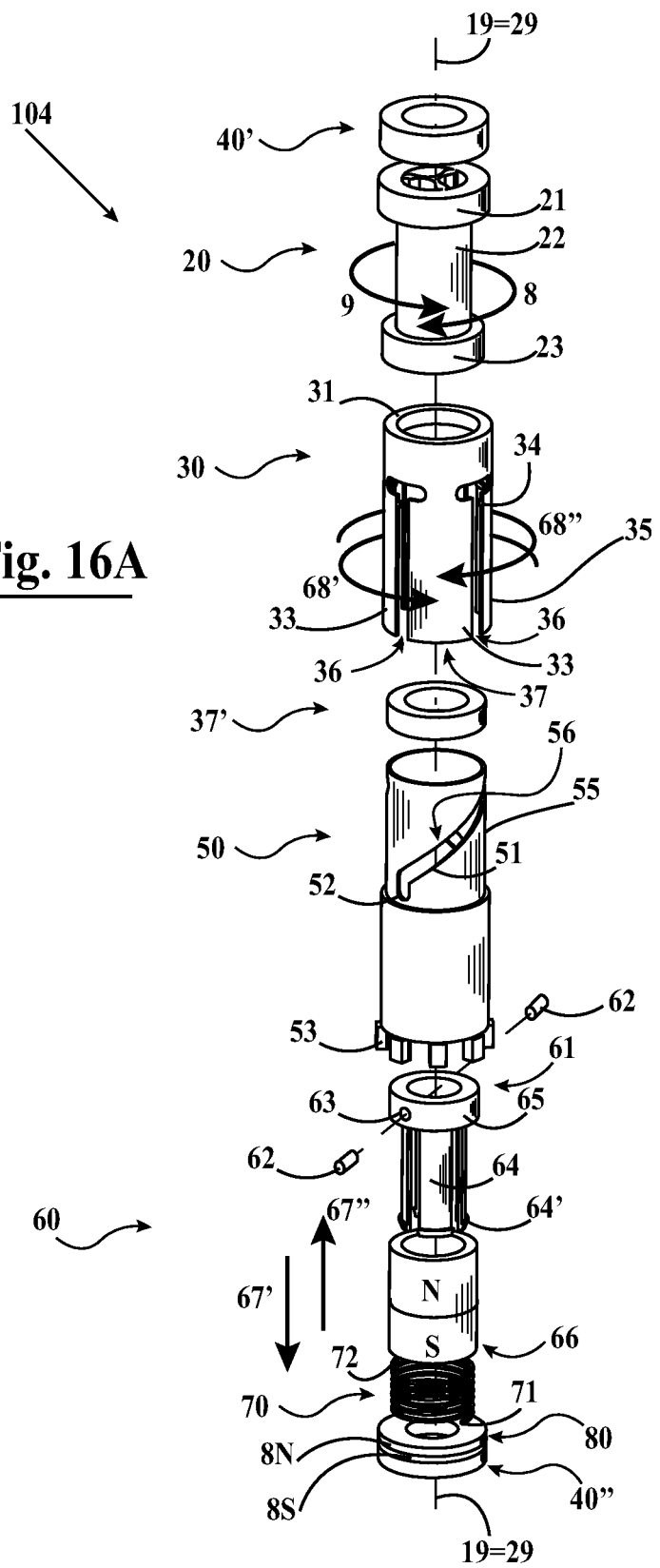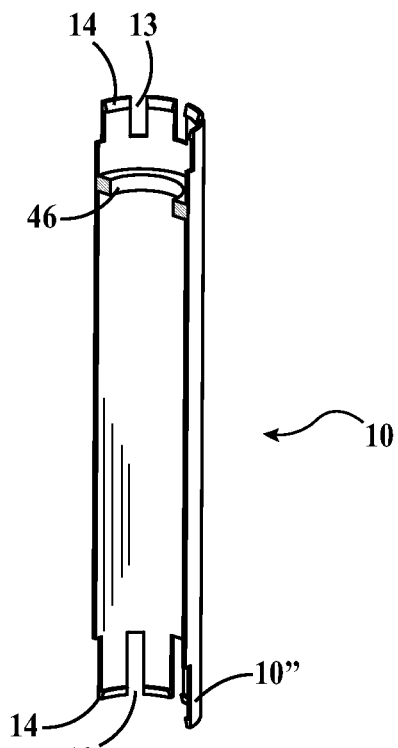
Fig. 16A
Fig. 16B

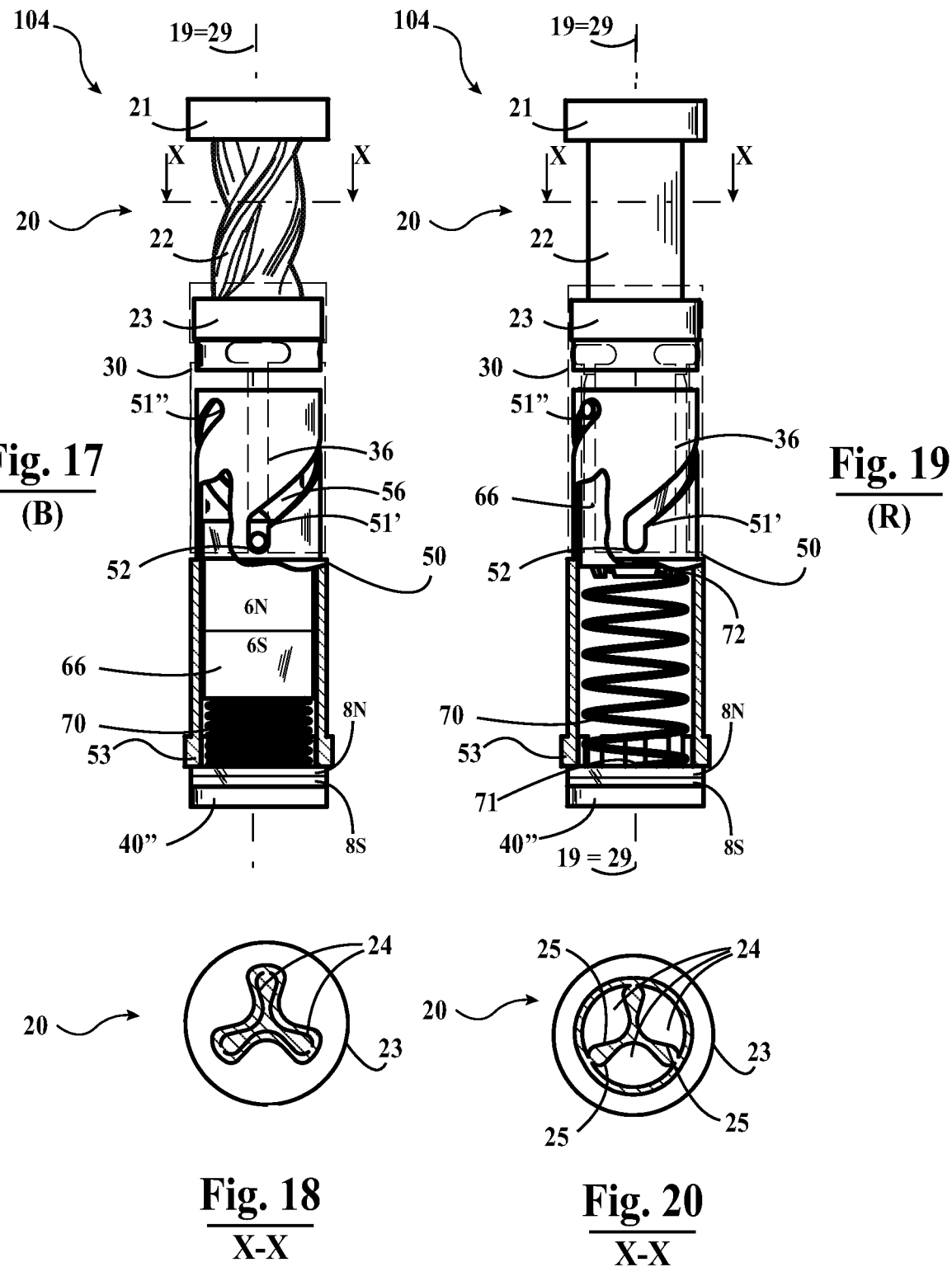

$\gamma = 180 - \theta_{17}$ $\gamma = -|180 - \theta_{18}|$ (B)

(R)

(B)

$\gamma = 180 - \theta_{17}$ (R)

$\gamma = -|180 - \theta_{18}|$

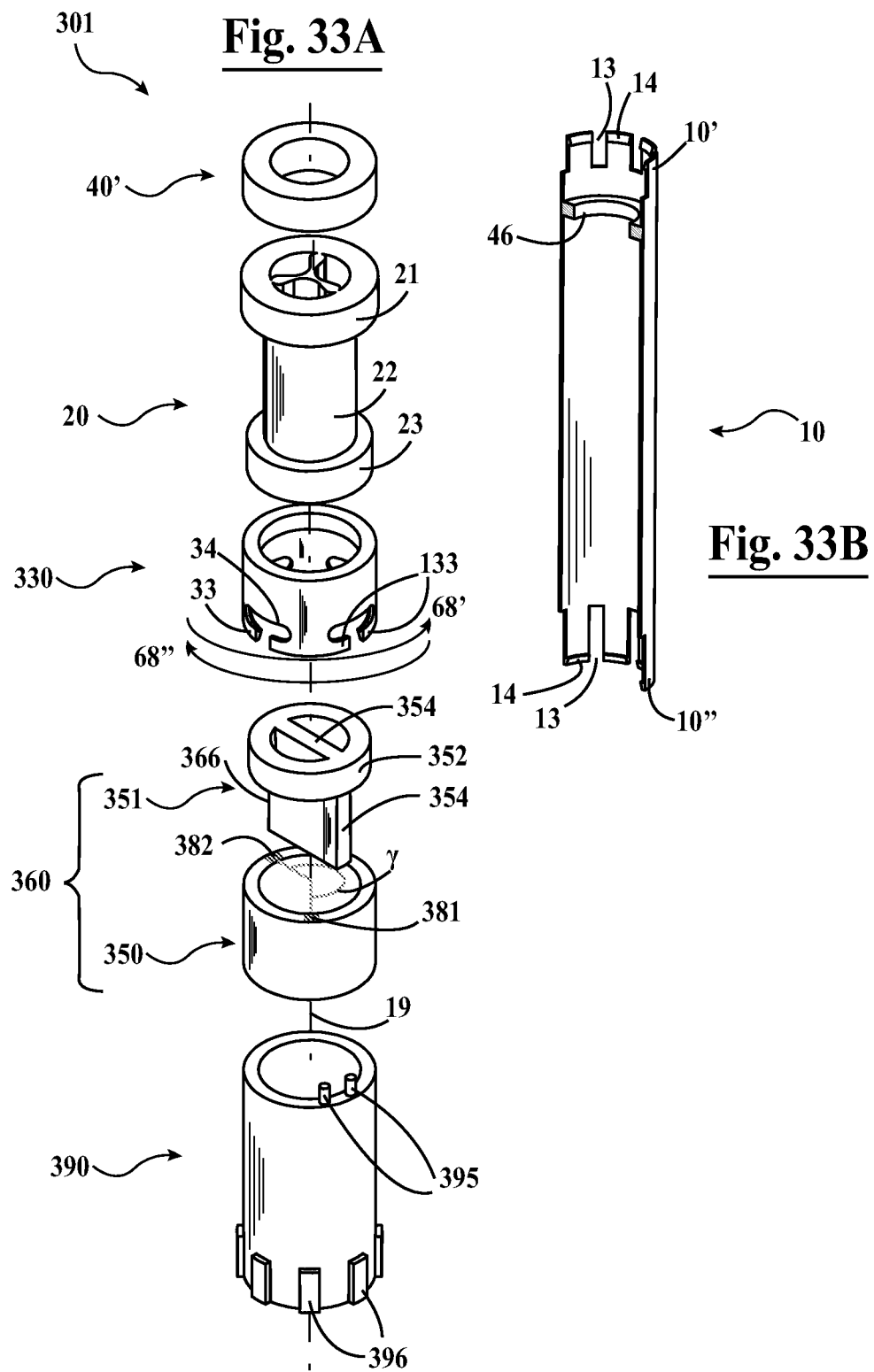

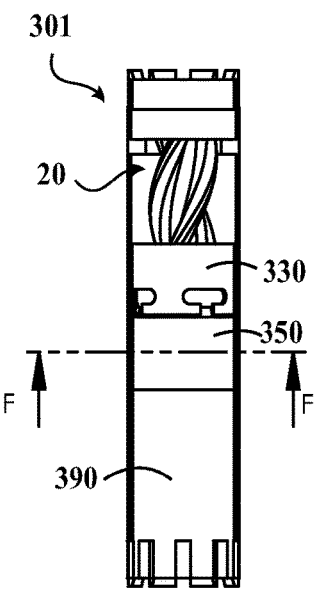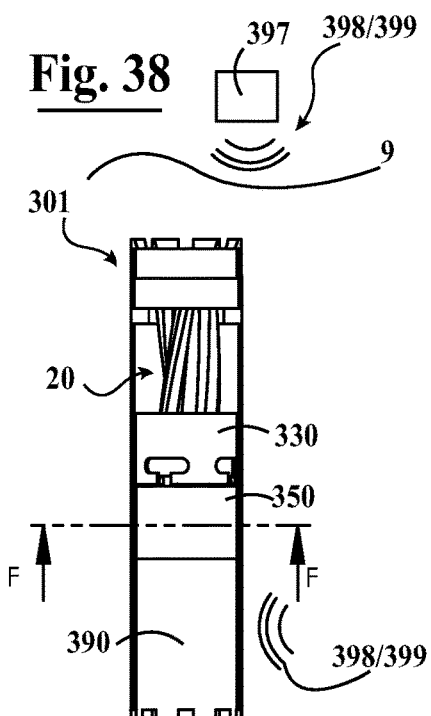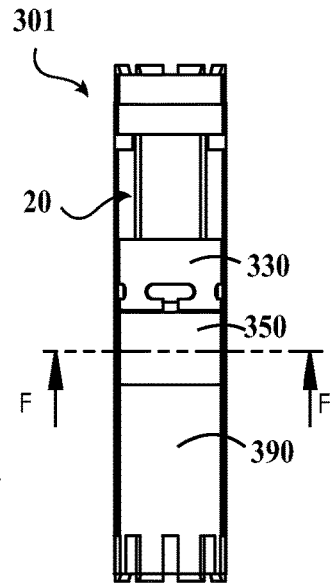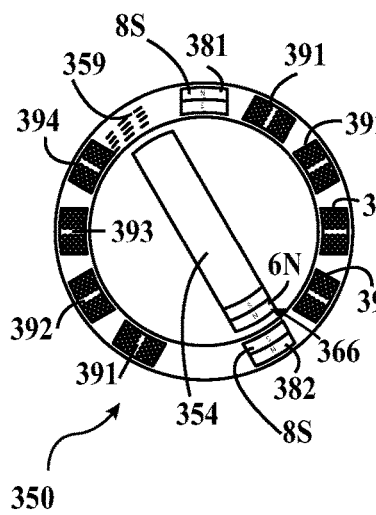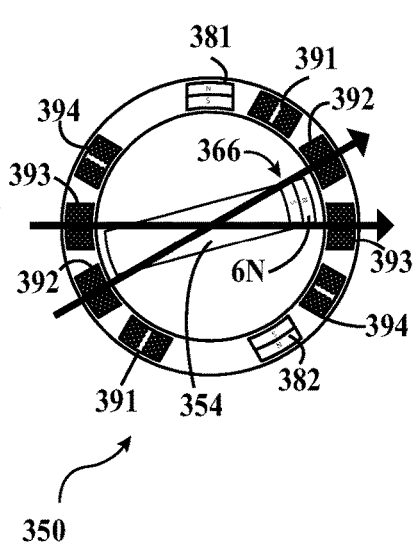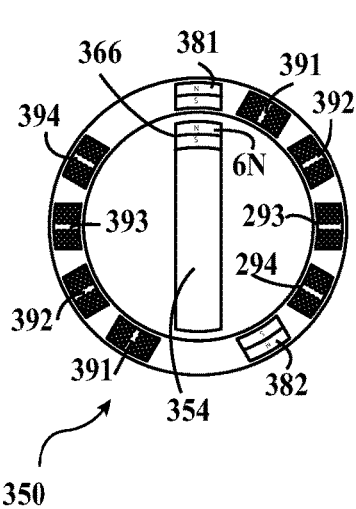

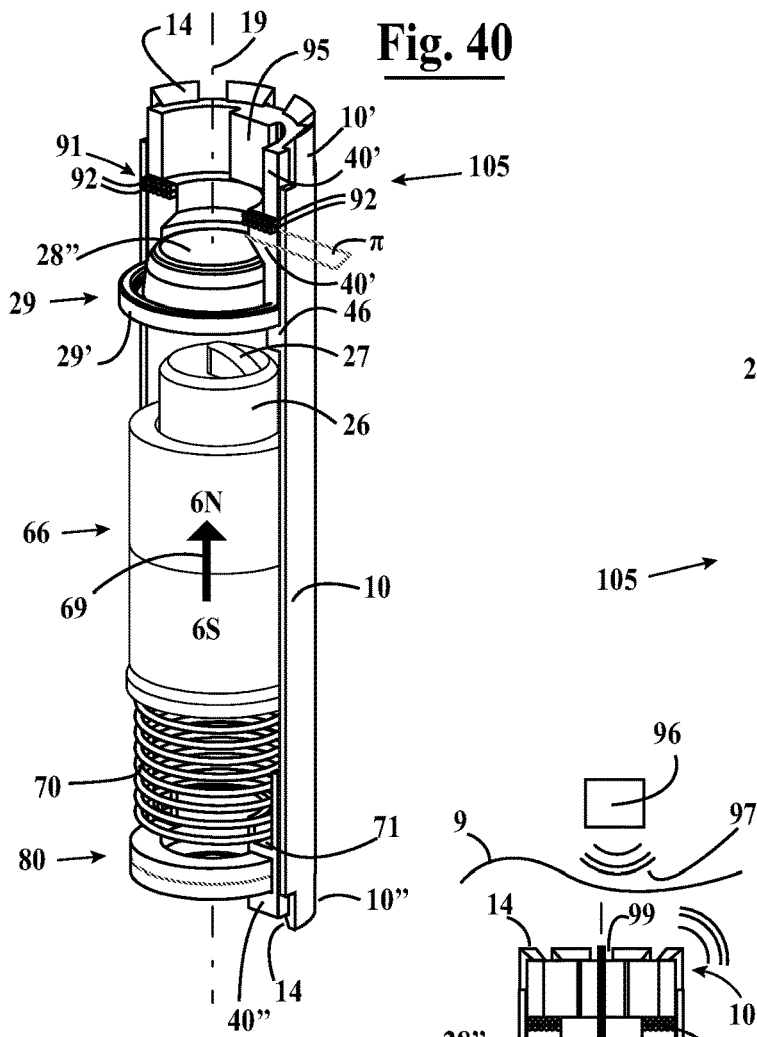
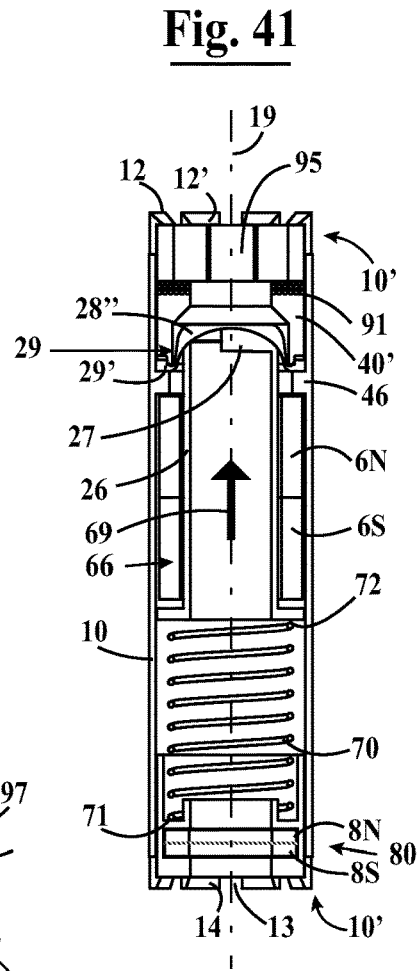
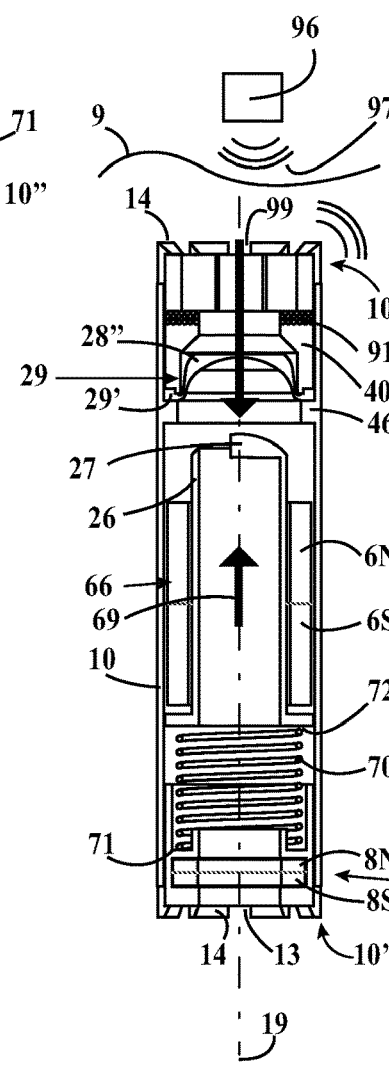
Fig. 40
Fig. 41
Fig. 42

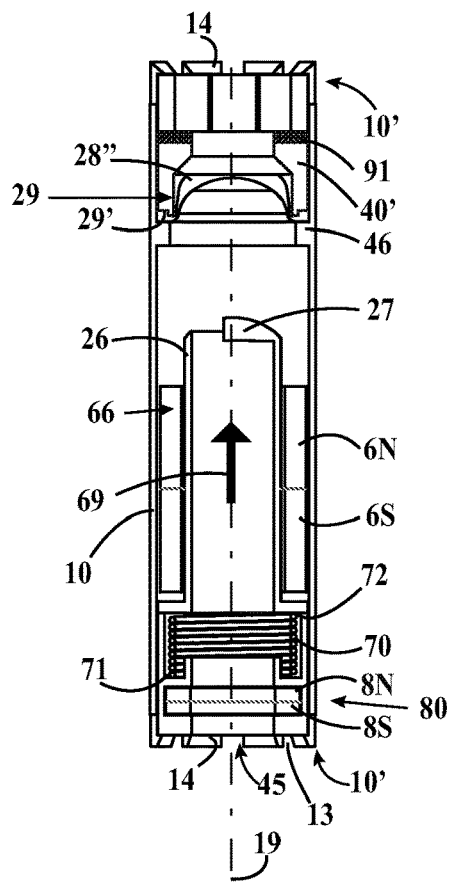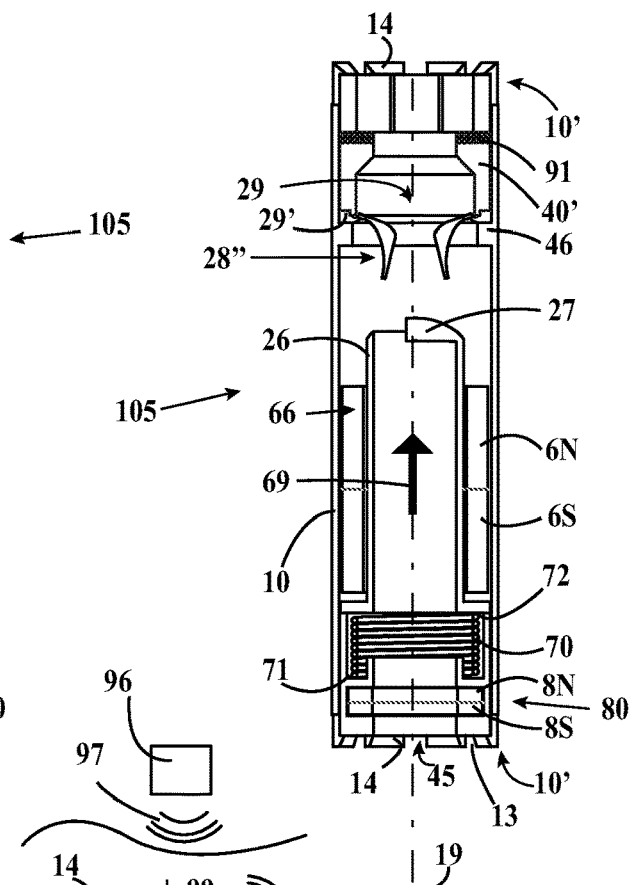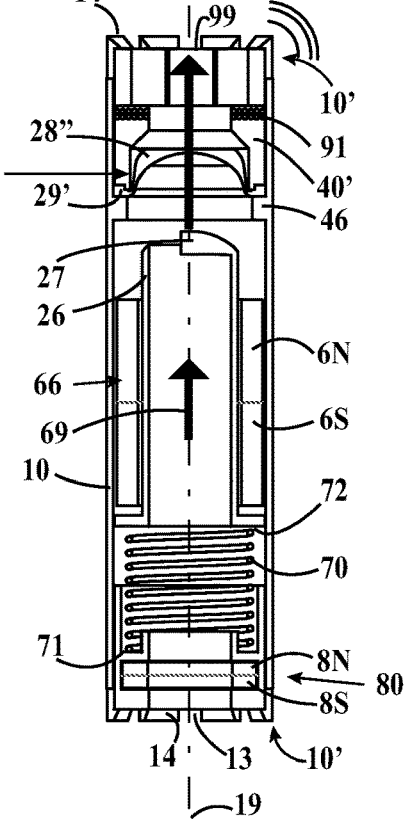

URETHRAL ARTIFICIAL SPHINCTER WITH BISTABLE ACTUATION SYSTEM

FIELD OF THE INVENTION

The present invention relates to an artificial sphincter for endourethral and extraurethral implants, in particular for treating patients who suffer from urinary incontinence.

TECHNICAL FIELD AND TECHNICAL PROBLEMS

Many types of artificial urethral sphincters are known for treating urinary incontinence. They are used when such remedies as outpatient therapy, the pharmacologic therapy and the pelvic re-education are not successful. Artificial urethral sphincters have been also used as an alternative to traditional surgery techniques, by which the bladder supporting structure are reconstructed.

WO 2013/144770 describes endourethral sphincters comprising a container and, inside it, a valve element and a safety element for preventing an unwanted opening of the sphincter. Preferably, the valve element comprises a cap shell comprising radial sectors configured to move away from one another upon increase of the patient's abdominal pressure. In an exemplary embodiment preferred for its reliability, the safety element comprises an abutment member or piston that, in block/release configurations, is arranged to be close/at a distance from the concave surface of the shell, thus preventing it from opening/allowing it to open, the piston being controlled by a return spring and having a magnetic portion, so that it can be moved to the release configuration by the action of a manoeuvre magnet suitably located near the abdomen.

U.S. Pat. No. 6,409,656 B1 describes an extraurethral artificial sphincter comprising a T-shaped container, in which the arms of the T form a support for receiving such a duct as a patient's urethra, whereas the stem of the T houses a valve unit in which a magnetic field-sensitive element, in particular a permanent magnet, is slidably mounted along the stem with the possible magnetic axis arranged longitudinally, and is integrally connected to the two end portions of a strap mounted to form a clasp element about a portion of the section the urethra. A resilient axial element is also provided, for example in the form of a bellows, mounted with the ends connected to the container and to the slidable element, respectively. The length of the clasp element and the stiffness of the bellows are selected in such a way that, in the absence of any significant external magnetic fields, the urethra is tightened between the clasp element and a surface of the support, which stops the flow of urine. In order to allow a flow of urine, it is provided that the patient positions a permanent magnet close to the sphincter, and orients it in so as to repel the sliding element, if also the latter is a permanent magnet, to resist the action of the bellows and to push the sliding element, thus removing the constriction the clasp element produces on the urethra.

The devices of WO 2013/144770 and U.S. Pat. No. 6,409,656 B1 require that the manoeuvre magnet remains positioned close to the abdomen until the end of the micturition, which makes their use uncomfortable. Other endourethral artificial sphincters are described in WO 2004/037134, and have substantially the same drawbacks.

WO 2014/205271 describes an artificial sphincter comprising a ring in which a fixed portion to be integrally positioned on the external wall of the urethra, and a movable second portion to be arranged in such a way that the movable portion can be approached to and moved away from the first portion, in order to tighten the urethra on the first portion and to release it, in a closed position and in an open position, respectively. The movable portion is integrally connected to an actuation magnetic piston slidably arranged in a cylindrical chamber at one end of which, opposite to the ring, a metal element is arranged that is capable of retain the magnet and maintain therefore the second portion in the closed position, while the open position can be maintained by taking advantage of the elasticity of the urethra and of the pressure of the urine contained therein, provided the piston has been moved towards this position by with an external magnet.

Grunemberger A. D. et al. "A magnet system for urethral closure in females", J. Biomed. Eng. 1984, Vol. 6, April, pp. 102-106, describes an artificial sphincter for a patient, such device comprising a fixed first magnet to be implanted on a patient's pubic bone and a second magnet to be positioned opposite to the first magnet with respect to the urethra, with a pole oriented towards the pole of the same name of the first magnet, and configured to translate towards/away from the first magnet, in order to selectively tighten/release the urethra. However, no device is described to cause the second magnet to translate.

U.S. Pat. No. 3,731,670 describes a valve, i.a. for the urethra, in which a tubular container includes a magnetic field-sensitive closing spherical element that is small enough to be freely displaced within the container, and has housings at both end portions arranged to receive and to magnetically retain the closing element, one only of the housings being arranged to block the flow of a fluid in the presence of the closing element, which is not the case for the other end housing, thus defining a closed position and an opening position, respectively, of the closing element. The valve opening and closing can be operated by an external magnet, powerful enough and at a distance short enough to drag the closing element away from a housing to an appropriate distance so that it can be attracted towards the opposite housing. In some exemplary embodiments, the closing element itself can be a magnet, besides or as an alternative to the two end housings.

US 2007/0276342 describes an endourethral artificial sphincter, an exemplary embodiment of which comprises a duct and a valve unit consisting of at least one couple of discs coaxially arranged within the duct, one fixedly and the other rotatably arranged about a longitudinal axis of the duct, both the discs having respective openings arranged so that of the opening of the mobile disc, by a rotation thereof, can overlap/be offset with respect to the opening of the fixed disc, which defines open/closed relative position for the artificial sphincter. The discs have axially oriented magnets that are arranged in such a way that, due to mutual repulsion, and in the absence of any external magnetic fields, the movable disc moves to the closed position. In order to open the sphincter, the patient can arrange such a magnetic source as a permanent magnet, in order to exceed the forces that are exerted between the discs, and to bring the movable disc to the open position, maintaining the external magnet proximate to the device as long es he wants that the sphincter remains open, in other words, this sphincter does not provide a bistable actuation.

SUMMARY OF THE INVENTION

It is therefore a feature of the invention to provide an artificial, magnetically operated sphincter for the urethra, whose operation does not require to keep an external manoeuvre magnet near the implant for the whole duration of the micturition, and that is therefore more practical and hygienic to use.

In a first exemplary embodiment of the invention, these and other objects are achieved by an artificial sphincter comprising:
- a container having a longitudinal axis, the container configured to be connected to a wall of a patient's urethra;
- a valve unit arranged within the container, and configured to reversibly move between:
  - a release configuration, in which the valve unit is arranged to allow a passage of urine through the artificial sphincter, and
  - a block configuration, in which the valve unit is arranged to prevent the passage of urine through the artificial sphincter;
- a stabilization magnet having poles arranged along a first magnetic axis, said stabilization magnet arranged integral to the container with the first magnetic axis parallel to the longitudinal axis,
- an actuation magnet having poles arranged along a second magnetic axis, parallel to the longitudinal axis,
- wherein the actuation magnet is slidably arranged within the container, in order to change its own distance from the stabilization magnet along the longitudinal axis and to responsively change the magnetic force between the actuation magnet and the stabilization magnet;
- wherein the actuation magnet is connected to the valve unit in such a way that a translation movement of the actuation magnet under the effect of a manoeuvre magnet positioned at a predetermined distance from the actuation magnet, causes the valve unit to move between the release configuration and the block configuration,
- an resilient element, for example a cylindrical helical spring, said resilient element having a first end integral to the container and a second end, opposite to the first end, connected to the actuation magnet, so that the actuation magnet receives a resilient force responsive to its own position along the container, wherein the resilient element, the actuation magnet and the stabilization magnet are arranged in such a way that:
- the magnetic force has a direction opposite to the resilient force;
- the magnetic force has an intensity higher than the resilient force when the actuation magnet is distanced less than a predetermined equilibrium distance from the stabilization magnet;
- the magnetic force has an intensity lower than the resilient force when the actuation magnet is distanced more than the equilibrium distance from the stabilization magnet, such that, by arranging the actuation magnet at a distance shorter/longer than the equilibrium distance from the stabilization magnet, the actuation magnet maintains/brings the valve unit in the release/block configuration.

This way, by arranging a manoeuvre magnetic element, such as a permanent magnet, that can create an external magnetic field of a predetermined intensity, outside the patient's body and proximate to the region where the artificial sphincter is implanted, in particular proximate to the perineum region, with its magnetic axis oriented in the same way as/in the opposite way with respect to the actuation magnet, the actuation magnet receives a manoeuvre magnetic force that, composed with the stabilization magnetic force, can displace the actuation magnet from the position corresponding to the release configuration to the position corresponding to the block configuration, or vice-versa, thus providing a bistable actuation of the artificial sphincter.

In a first modification of the sphincter according to the first exemplary embodiment, suitable for an extraurethral implant, i.e. in which the container is configured to be connected outside of the urethra,
- the container comprises a main body and a cover at an end portion thereof, and is configured to be crossed by a segment of the urethra at the end portion;
- the valve unit comprises a slidable stopper slidably arranged within the container, the actuation magnet integral to the slidable stopper, such that, when the actuation magnet is in an advanced position, a stopper abutment element of the slidable stopper engages with the cover, so as to press and close the segment of urethra, so that the urine cannot flow through the urethra, whereas, when the actuation magnet is in a retracted position, the stopper abutment element is at such a distance from the cover that the segment of urethra can have an open configuration, and the urine can flow therethrough.

In other modifications of the sphincter according to the first exemplary embodiment, suitable for endourethral implant, i.e. in which the container is configured to be internally fixed to the urethra,
- the valve unit comprises a slidable stopper slidably arranged within the container, the actuation magnet integral to the slidable stopper,
- the slidable stopper has a stopper abutment element, and the artificial sphincter comprises a sealing housing arranged to fluid-tightly engage with the stopper abutment element when the actuation magnet is in an advanced position along with the slidable stopper, obtaining the block configuration.

Among these other modifications, in a second modification of the first exemplary embodiment, the sealing housing is a sealing element formed in an inner wall of the container, and is configured to directly engage with the stopper abutment element.

Among these other modifications, in a third modification of the first exemplary embodiment, the sealing housing is made as a resilient shell portion of a valve element, having at least one through notch, this resilient shell portion configured to move:
- from a closed configuration, in which the resilient shell portion has a convex shape opposite to the slidable stopper, and forms a diaphragm, such that a urine pressure on the resilient shell portion maintains the through notch closed;
- an open configuration, in which the resilient shell portion has a concave shape opposite to the convex shape, where the through notch is deformed and open, and is configured to allow a passage of urine, in the convex shape, the resilient shell portion configured to bear the urine pressure up to a pressure limit, above which the resilient shell portion collapses into the concave shape, so as to allow the flow of the urine through the through notch,
and the stopper abutment element is configured to prevent the resilient shell portion from moving from the closed configuration to the open configuration when the stopper abutment element engages with the resilient shell portion.

This way, the slidable stopper works as a safety element configured to prevent the valve element from moving from the closed configuration to the open configuration, in the block configuration, and, accordingly, to avoid an unwanted flow of urine through the valve element. In particular, this serves to prevent actuation of the structure by a sudden increase of pressure within the bladder, which may occur due to a patient's cough or effort of various kinds. The slidable stopper is also configured to allow the valve element to move from the closed configuration to the open configuration, in the release configuration, and then to allow urine to flow out, under a given intra-bladder pressure and preferably under a deliberate abdominal pressure increase.

The resilient element works as an elastic return element, in order to stably keep the safety element in the block configuration. More in detail, the elastic constant of the spring can be selected so that the deformable valve element cannot move from the closed configuration to the open configuration whatever sudden urine pressure increase may occur.

In a further, fourth modification of the first exemplary embodiment, which is also suitable for an endourethral implant, the valve unit comprises a torsionally compliant tubular body with an own longitudinal axis parallel to the longitudinal axis, and comprising:
 a first end portion and a second end portion, the first end portion integral to the container;
 a central portion torsionally compliant about the second longitudinal axis, wherein an opening/closing torsional deformation of the central portion brings the torsionally compliant tubular body:
  from the release configuration, in which the torsionally compliant central portion defines a passageway in the torsionally compliant tubular body along the longitudinal axis of the tubular body,
  to the block configuration, in which inner walls of the torsionally compliant central portion are in contact with one another so as to completely block the passageway in at least one part of the central portion,
 /or vice-versa,
wherein said artificial sphincter also comprises:
 an actuation unit comprising:
  said actuation magnet;
  a hollow cylindrical guide element arranged within and integral to the container, wherein said guide element has a first channel having a helical portion;
  a rotatable actuation cylinder, rotatably arranged within the container about a longitudinal axis thereof, and having:
   an end part integral to the second end portion of the torsionally compliant tubular body;
   a channelled part with a linear second channel, wherein the channelled part telescopically engages with the guide element at the first channel;
  at least one outer radial protrusion integral to the actuation magnet and engaging with both the first channel and the second channel;
such that a translation movement of the actuation magnet brings the outer radial protrusion from a first position to a second position along the helical portion of the first channel, thus causing the opening/closing torsional deformation and moving the valve unit from the release configuration to the block configuration, or vice-versa.

In particular, the first channel comprises a linear longitudinal end portion adjacent to the position that, among the first and the second positions, correspond to the block configuration.

The artificial sphincter can comprise a manoeuvre electromagnet with a control unit, in particular the electromagnet is a winding in which coils of an electrically conductive material are arranged on respective planes substantially perpendicular to the longitudinal axis of the container, and is arranged to create a manoeuvre magnetic field whose manoeuvre magnetic axis is substantially parallel to the longitudinal axis, the control unit configured to supply an electric current to the manoeuvre electromagnet, the electric current having:
 a first or a second direction, selected in such a way that the magnetic axis of the manoeuvre magnetic field has the same orientation as or the opposite orientation with respect to the second magnetic axis of the actuation magnet, so that the latter receives a manoeuvre magnetic force having the same direction as or the opposite direction, respectively, with respect to the magnetic force and, accordingly, the opposite direction or the same direction, respectively, with respect to the resilient force;
 an intensity selected in such a way that the manoeuvre magnetic force, having the same direction as or the opposite direction with respect to the magnetic force, causes the actuation magnet to carry out a translation movement so as to bring the actuation magnet from the retracted position to the advanced position, respectively or vice-versa, causing the valve unit to move from the release configuration to the block configuration, respectively, or vice-versa.

In a second exemplary embodiment of the invention, the above mentioned objects are achieved by an artificial sphincter comprising:
 a container having a longitudinal axis, the container configured to be connected to a wall of a patient's urethra;
 a valve unit arranged within the container, and configured to reversibly move between:
  a release configuration, in which the valve unit is arranged to allow a passage of urine through the artificial sphincter;
  a block configuration, in which the valve unit is arranged to prevent the passage of urine through the artificial sphincter;
 a stabilization magnet having poles arranged along a first magnetic axis, said stabilization magnet arranged integral to the container with the first magnetic axis transversally arranged with respect to the longitudinal axis, wherein the stabilization magnet is arranged with an own predetermined reference pole in an angular reference position within an actuation angular sector defined between a first angular position and a second angular position with respect to the container;
 an actuation magnet having poles arranged along a second magnetic axis, which is transversally arranged with respect to the longitudinal axis,
 wherein the actuation magnet is rotatably arranged with respect to the stabilization magnet in order to responsively change a magnetic moment between the actuation magnet and the stabilization magnet responsive to the rotation of the actuation magnet about a longitudinal axis,
 wherein the actuation magnet is connected to the valve unit in such a way that a rotation of the actuation magnet, under the effect of a manoeuvre magnet positioned at a predetermined distance from the actuation magnet, shifts the actuation pole between the first angular position and the second angular position, thus causing the valve unit to move between the release configuration and the block configuration, respectively, wherein the actuation magnet is rotatably arranged with an own actuation pole having the same name as the reference pole of the stabilization magnet between the first angular position and the second angular position, within the actuation angular sector,
such that, by causing the actuation magnet to carry out a rotation movement comprising a displacement of the actuation pole starting from the first angular position or from the second angular position, the magnetic moment:
  recalls the actuation magnet and brings the actuation pole back to the first angular position or to the second angular position, respectively, so as to maintain stably the valve unit in the release configuration or in the block configuration, respectively or
  brings the actuation pole of the actuation magnet to the second angular position or to the first angular position, respectively, so as to maintain stably the valve unit in the block configuration or in the release configuration, respectively,
  according to whether, by the rotation, the actuation pole is brought beyond or is not brought beyond the angular reference position, respectively.

This way, by arranging a manoeuvre magnetic element that can create an external magnetic field of a predetermined intensity, for example a permanent magnet, outside of the body, close to the abdomen, with the magnetic axis oriented in the same way/in the opposite way with respect to the actuation magnet, the actuation magnet receives a manoeuvre magnetic moment that, composed with the magnetic stabilization moment, can displace the actuation magnet from the angular position corresponding to the release configuration or to the block configuration to a position beyond the angular reference position, and then the stabilization moment brings the actuation magnet to the angular position corresponding to the block configuration or to the release configuration, respectively, thus providing a bistable actuation of the artificial sphincter.

In a first modification of the sphincter of the second exemplary embodiment suitable for endourethral implant, i.e. in which the container is configured to be internally fixed to the urethra, the valve unit comprises a tubular body having the features of the tubular body of the fourth modification of the first exemplary embodiment, and, moreover,
  the artificial sphincter also comprises an actuation cylinder rotatably arranged within the container about the first longitudinal axis, and comprising an abutment member connected peripherally to the actuation cylinder at a predetermined abutment angle with respect to the actuation pole, in particular the abutment member is arranged in an angular position at the actuation pole of the actuation magnet,
  the actuation magnet is integral to the actuation cylinder,
  the actuation cylinder is pivotally constrained at the second end portion of the torsionally compliant tubular body in such a way that, when the abutment member abuts against a first/second abutment element, the tubular body is in the block/release configuration.

In a second modification of the sphincter according to the second exemplary embodiment, suitable for an extraurethral implant,
  the container comprises a main body and a cover at an end portion thereof, and is configured to be crossed by a segment of the urethra at the end portion;
  the artificial sphincter also comprises:
    a hollow cylindrical guide element coaxially arranged within and integral to the container, said guide element having a linear channel parallel to the longitudinal axis and arranged at a predetermined angular distance from the reference pole of the stabilization magnet;
    an actuation cylinder comprising a helical channel having an angular amplitude equal to the amplitude of the actuation angular sector about its own axis, the actuation cylinder rotatably engaging with the cylindrical guide element and integral to the actuation magnet;
  the valve unit comprises a slidable stopper movably arranged within the actuation cylinder, the slidable stopper having an outer radial protrusion that engages with both the linear channel and the helical channel, the slidable stopper arranged in such a way that, when the actuation pole is in the first angular position, a stopper abutment element of the slidable stopper is at a predetermined distance from the cover, in order to allow the segment of urethra to have an open configuration, and to allow the passage of urine, whereas, when the actuation pole is located in the second angular position, the stopper abutment element of the slidable stopper engages with the cover, so as to press and close the segment of urethra, so that the urine cannot flow through the urethra.

In a third exemplary embodiment of the invention, the above mentioned objects are achieved by an artificial sphincter comprising:
  a container having a longitudinal axis, the container configured to be connected to a wall of a patient's urethra;
  a valve unit arranged within the container, and configured to move:
    from a release configuration, in which the valve unit is arranged to allow a passage of urine through the artificial sphincter;
    to a block configuration, in which the valve unit is arranged to prevent the passage of urine through the artificial sphincter;
  and vice-versa,
  a motor comprising:
    a stator co-axial and integral to the container;
    a rotor rotatably arranged within the stator, and comprising an actuation magnet having a reference pole, for example the pole north, facing an inner surface of the stator,
  wherein the stator comprises:
    two stabilization magnets angularly spaced apart from each other by a predetermined actuation angle having a vertex on the longitudinal axis, the two stabilization magnets having a pole of name opposite to the reference pole of the actuation magnet oriented inwards of the stator, and the other pole oriented outwards of the stator, in the previous example having i.e. the pole south oriented inwards of the stator and the pole north oriented outwards;
    a plurality of manoeuvre electromagnets, in particular a plurality of windings of coils of an electrically conductive material arranged on planes tangent to respective cylindrical surfaces coaxial to the stator;
  wherein the manoeuvre electromagnets are arranged in such a way that the reference pole of the actuation magnet faces each manoeuvre electromagnets, when the rotor is in a respective angular position;
  wherein the actuation magnet is connected to the valve unit in such a way that, when the reference pole of the actuation magnet is facing a first/second stabilization magnet of the two stabilization magnets, the valve unit is respectively in the release/block configuration;

a control unit configured to selectively and consecutively supply a manoeuvre electric current to the manoeuvre electromagnets, the manoeuvre electric current having an intensity selected in such a way that the rotor rotates, causing the reference pole of the actuation magnet to consecutively face the manoeuvre electromagnets, such that, by selectively and consecutively supplying the manoeuvre electric current to the manoeuvre electromagnets, the rotor rotates, thus bringing the reference pole from a position facing the first stabilization magnet to a position facing the second stabilization magnet, or vice-versa, and causing the valve unit to move from the release configuration to the block configuration, or vice-versa.

In a fourth exemplary embodiment of the invention, an artificial sphincter comprises:

a container having a longitudinal axis, the container comprising a main body and a cover at an end portion thereof, and configured to be crossed by a segment of a patient's urethra at the end portion;

a hollow cylindrical guide element coaxially arranged within and integral to the container, wherein said guide element has a first channel parallel to the longitudinal axis, the first channel having a linear portion parallel to the longitudinal axis and first and second circumferential end portions arranged at a predetermined distance from each other;

an actuation cylinder having a second helical channel having a predetermined height, measured along the longitudinal axis, at least equal to the distance between the first circumferential portion and the second circumferential portion of the first channel, the actuation cylinder rotatably engaging with the cylindrical guide element, with the second channel arranged axially within the length of the first linear channel;

an actuation magnet having poles arranged along a magnetic axis, the actuation magnet arranged integral to the actuation cylinder with the magnetic axis transversally arranged, in particular perpendicularly arranged, with respect to the longitudinal axis;

a valve unit comprising a slidable stopper movably arranged within the actuation cylinder, the slidable stopper having an outer radial protrusion that engages with both the first channel and the second channel; the slidable stopper arranged in such a way that, when the outer radial protrusion is in the first circumferential end portion of the second channel, a stopper abutment element of the slidable stopper is at a predetermined distance from the cover, in order to allow the segment of urethra to have an open configuration, and to allow the passage of urine, whereas, when the outer radial protrusion is in the second circumferential end portion of the second channel, the stopper abutment element engages with the cover, so as to press and close the segment of urethra, so that the urine cannot flow through the urethra.

BRIEF DESCRIPTION OF THE DRAWINGS

The invention will be now shown with the description of some exemplary embodiments, exemplifying but not limitative, with reference to the attached drawings, in which:

FIGS. 3A-3E diagrammatically show an artificial sphincter according to a first exemplary embodiment of the invention, in subsequent steps of an opening-closing cycle;

FIG. 3F diagrammatically shows the forces that act on an actuator of the sphincter of FIGS. 3A-3F;

FIG. 4 is a perspective view of an artificial extraurethral sphincter according to a first modification of the first exemplary embodiment, in which a portion of the container is removed;

FIGS. 5 and 6 are cross sectional views of the artificial sphincter of FIG. 4, in a block configuration and in a release configuration, respectively;

FIG. 7 is a perspective view of an artificial endourethral sphincter, in which a portion of the container is removed, according to a second modification of the first exemplary embodiment, in which a slidable stopper and a sealing housing integrally formed in an inner wall of the container are provided;

FIGS. 8 and 9 are cross sectional views of the artificial sphincter of FIG. 7, in a block configuration and in a release configuration, respectively;

FIGS. 16A and 16B are exploded perspective views of an artificial endourethral sphincter according to a fourth modification of the first exemplary embodiment, in which a torsionally compliant stopper is provided;

FIGS. 17 and 18 are a partial side cross sectional view and a cross sectional view, respectively, of the sphincter of FIGS. 16A and 16B, in a block configuration;

FIGS. 19 and 20 are a partial side cross sectional view and a cross sectional view, respectively, of the sphincter of FIGS. 16A and 16B, in a release configuration;

FIGS. 33A and 33B are exploded perspective views of an artificial endourethral sphincter according to a third exemplary embodiment of the invention, in which a torsionally compliant stopper is provided;

FIGS. 34, 35 and 36 are cross sectional views of the sphincter shown in FIGS. 33A and 33B, made at an actuation motor, in a block configuration, a release configuration, and a partial release configuration, respectively;

FIGS. 37, 38 and 39 are partial side cross sectional views corresponding to the views of FIGS. 34-36;

FIG. 40 is a perspective view of an artificial endourethral sphincter of the first exemplary embodiment, in particular in the third exemplary embodiment, in which a portion of the container is removed, including a manoeuvre magnet in the form of an electromagnet;

FIGS. 41-45 show side sectional views of the sphincter of FIG. 40, in subsequent steps of an opening-closing cycle;

DESCRIPTION OF A PREFERRED
EXEMPLARY EMBODIMENT

Figure 1:
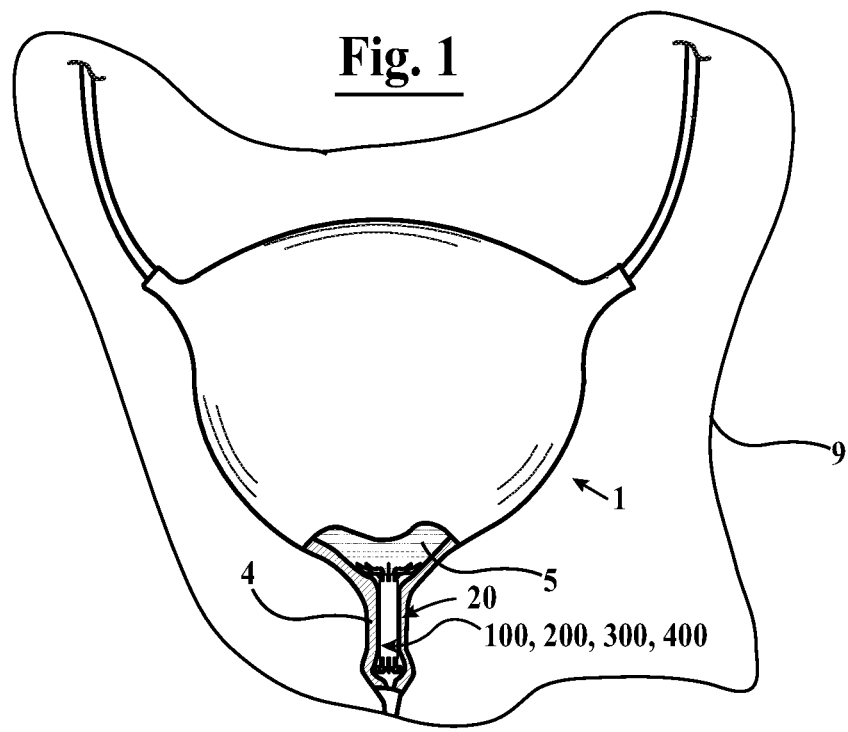
FIGS. 1 and 2 diagrammatically show sphincters respectively endourethral and extraurethral each connected to an internal wall and to an external wall, respectively, of a urethra.
Figure 2:
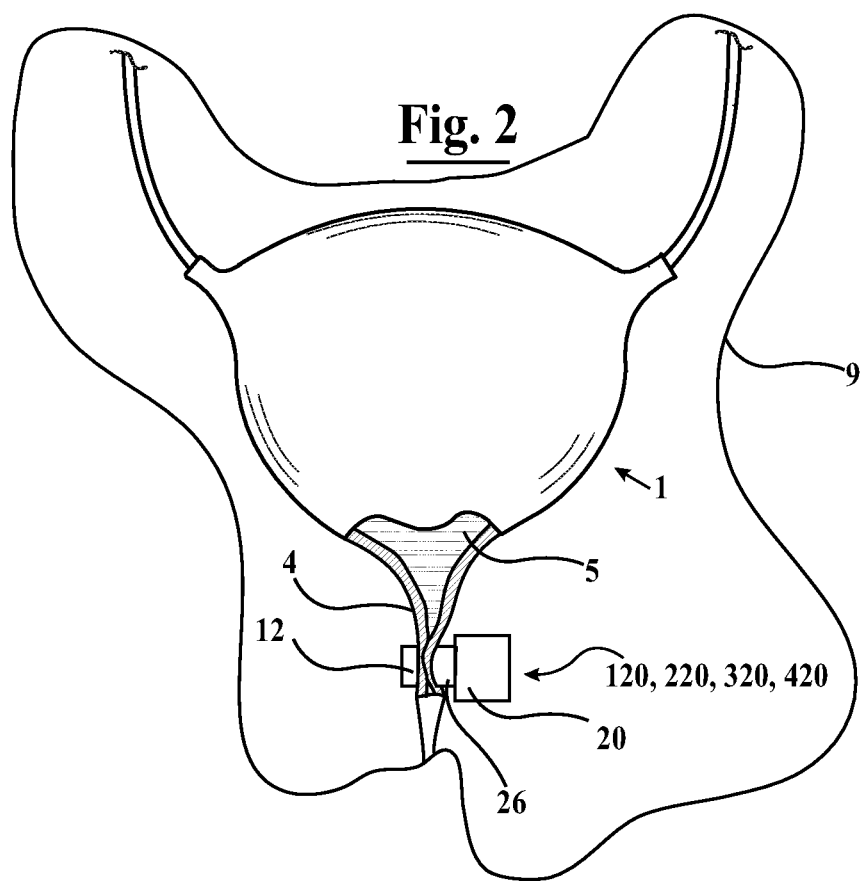

FIGS. 1 and 2 diagrammatically show endourethral and extraurethral artificial sphincters 100 and 120, respectively, i.e. sphincters configured to be implanted i.e. connected inside and outside of a urethra 4, respectively, each having of an own valve unit 20 to selectively provide release/block configurations of artificial sphincters 100,120 to allow/prevent the outflow of urine 5 contained within a patient's bladder 1 through urethra 4. Valve unit 20 of endourethral sphincter 100 is arranged to open/close an inner lumen. Instead, in the extraurethral sphincter 120, the valve unit comprises a slidable stopper 26 and a fixed cover 12 arranged to maintain inner size of/tighten urethra 4.

First Exemplary Embodiment

As diagrammatically shown in FIG. 3A, in a first exemplary embodiment, endourethral sphincter 100,120 comprises a container 10 configured to be connected to urethra 4. The container houses valve unit 20, which is configured to move from a release configuration R, to a block configuration B, and vice-versa. container 10 also houses a fixed stabilization magnet 80 and an actuation magnet 66 slidably arranged along the axis 19 of container 10, between a retracted position $d_R$ and an advanced position dB, with respective magnetic axes 89 and 69 arranged substantially parallel to the longitudinal axis 19 of container 10. With such an arrangement, stabilization magnet 80 creates a magnetic force $F_m$ acting on actuation magnet 66 responsive to position d of actuation magnet 66 along longitudinal axis 19, for example with respect to one end 10" of container 10. The diagram of FIG. 3F shows this relationship, which is typically non-linear with respect to distance d.

Magnetic axis of magnets 66, 80 means an oriented segment from respective South poles 6S,8S to respective North poles 6N,8N of each magnet. In the present exemplary embodiment, actuation magnet 66 and stabilization magnet 80 are cylindrical magnets, with the poles 6N,6S and 8N,8S, respectively, arranged along their own longitudinal axes, in other words actuation magnet 66 and stabilization magnet 80 are axial magnets.

Actuation magnet 66 is connected to valve unit 20, directly or by a mechanism, so that a translation movement 67',67" of actuation magnet 66 from retracted position $d_R$ to advanced position dB, or vice-versa, causes valve unit 20 to move from release configuration R to block configuration B.

Container 10 also houses a resilient longitudinal element 70, in particular a spring 70, for example a cylindrical helical spring connected by an own first end 71 to container 10 and connected by an opposite second end 72 to actuation magnet 66. When pulled/compressed, resilient longitudinal element 70 reacts by a resilient force $F_e$. With such an arrangement, actuation magnet 66 receives resilient force $F_e$, which also depends on position d along container 10, a typical linear relationship being established, as also shown in the diagram of FIG. 3F.

Resilient longitudinal element 70, actuation magnet 66 and stabilization magnet 80 are selected and arranged in such a way that magnetic force $F_m$ and resilient force $F_e$ acting on actuation magnet 66 are directed opposite to each other. For instance, in the case shown and in the modifications described below, stabilization magnet 80 is mounted at end 10" of container 10 opposite to an end 10' where valve unit 20 is arranged, stabilization magnet 80 and actuation magnet 66 are mounted with magnetic axes 89 and 69 oriented in the same way as each other, in other words magnets 80,66 are mounted with respective poles of opposite names facing each other, for example with the stabilization North pole of magnet 80 facing the south actuation pole magnet 66, as shown in FIG. 3A, so that force $F_m$ acting on actuation magnet 66 is attractive, i.e. it is positive with respect to the axis of FIG. 3A. On the other hand, resilient longitudinal element 70 is mounted so as to apply a negative resilient force $F_e$ on actuation magnet 66, in other words, resilient longitudinal element 70 is compressed and has a length shorter than its own rest length, when actuation magnet 66 is at a distance d shorter than $d_R$, so that resilient longitudinal element "pushes" actuation magnet 66 and tends to move it away from stabilization magnet 80.

Obviously, such a condition can also be obtained in a different way, not shown, in which first end 71 of the spring is fixed to the container at the same side as end 10', and in which the spring is stretched, i.e. it has a length longer than its own rest length, i.e. it is a traction spring, when actuation magnet 66 is at a distance d shorter than distance $d_R$. Still obviously, in another modification not shown, the condition in which forces $F_m$ and $F_e$ are opposite to each other can be obtained by arranging the actuation magnet and the stabilization magnet with the magnetic axes oriented opposite to each other, and arranging resilient longitudinal element 70 in a way that is evident for a skilled person, according to whether a traction spring or a compression spring is used.

As also shown in the diagram of FIG. 3F, resilient element 70, actuation magnet 66 and stabilization magnet 80 are selected and arranged also in such a way that magnetic force $F_m$ has an intensity higher than resilient force $F_e$ when actuation magnet 66 is located within a predetermined equilibrium distance d* from stabilization magnet 80, and that it has a lower intensity when actuation magnet 66 is located beyond equilibrium distance d*. This way, by arranging actuation magnet 66 within/beyond equilibrium distance d* with respect to stabilization magnet 80, actuation magnet 66 keeps/moves valve unit 20 in the release R/to block B configuration. In other words, the actuation magnet has two stable equilibrium positions, both position dB corresponding to the block configuration, and position $d_R$ corresponding to the release configuration, and the artificial sphincter is bistable.

With reference to FIGS. 3A-3E, the operation of artificial sphincter 100,120 will now be described. FIG. 3B shows sphincter 100 in block configuration B, where the magnetic attractive force $F_m$ between magnets 66 and 80 passes is higher than force $F_m$ that resilient longitudinal element 70 applies on actuation magnet 66. As shown in FIG. 3C, in order to bring valve unit to release position R, a manoeuvre magnet 90 is arranged so as to expose its own opposite pole to slidable actuation magnet 66, i.e., in this case, its own North pole. This way, an opening attractive manoeuvre force $F_M'$ is established between manoeuvre magnet 90 and slidable actuation magnet 66.

The features of manoeuvre magnet 90 and its position to cause artificial sphincter 100,120 to open are selected in such a way that the overall force acting on actuation magnet 66, i.e. the resultant of forces $F_e, F_M', F_m$ acting on actuation magnet 66 is oriented towards end 10" of container 10, so as to cause actuation magnet 66 to translate in this direction, moving valve element 20 away from block condition B. In other words, as also shown in the diagram of FIG. 3F, the magnitude of the overall attractive force $F_M' + F_m$ applied by two magnets 80,90 on slidable actuation magnet 66 is higher than the magnitude of the force of spring 70, so that slidable actuation magnet 66 is brought from position dB, corresponding to the block configuration, to any position d' beyond equilibrium distance d* (of >d*). In position d', attractive force $F_m$, exerted on slidable actuation magnet 66 by stabilization magnet 80 alone is higher than resilient force $F_e$. Therefore, as FIG. 3d diagrammatically shows, even if manoeuvre magnet 90 is removed, i.e. is moved away indefinitely from extraurethral sphincter 100,120, slidable actuation magnet 66 moves back and remains in position $d_R$, and valve unit 20 remains in the release configuration of FIG. 3D.

As FIG. 3E diagrammatically shows, manoeuvre magnet 90 is used again to return artificial sphincter 100,120 to the block configuration, but this time is positioned so as to expose its own pole of the same name to slidable actuation magnet 66, i.e., in this case, South pole 9S. This way, a repulsive magnetic force $F_M''$ is established between manoeuvre magnet 90 and slidable actuation magnet 66 in such a way that, with the prefixed features of manoeuvre magnet 90, the overall force acting on slidable actuation magnet 66, i.e. the resultant of forces $F_e, F_M'', F_m$, is a repulsive force, i.e. a force directed towards end 10' of container 10, so as to cause actuation magnet 66 to translate in this direction, moving valve element 20 away from release configuration R to any position d'', d''<d*, where resilient force $F_e$ is higher than attractive force $F_m$ exerted on actuation magnet 66 by stabilization magnet 80 alone. Therefore, as FIG. 3d diagrammatically shows, once manoeuvre magnet 90 has been moved away from extraurethral sphincter 100,120, slidable actuation magnet 66 moves back and remains in position dB, and valve unit 20 remains in the block configuration of FIG. 3B.

In a first modification of the first exemplary embodiment of FIGS. 4-6, in an artificial extraurethral sphincter 101, container 10 comprises a main body 11 and a cover 12 at end portion 10' thereof, and is configured to be crossed by a segment of urethra 4 at end portion 10'. Valve unit 20 comprises a slidable stopper 26 slidably arranged within container 10, to which preferably ring-shaped actuation magnet 66 is integrally connected, and has a stopper abutment element 27. When actuation magnet 66 is in the advanced position (FIGS. 4 and 5), the abutment element engages with cover 12, so as to press and close segment of urethra 4, and stop the flow of urine. On the other hand, when actuation magnet 66 is in the retracted position (FIG. 6), stopper abutment element 27 is arranged at a predetermined distance from the cover, so as to release segment of urethra 4, and allow the flow of urine 5 therethrough.

Stabilization magnet 80 preferably has the shape of a ring, and can be fixed to end 10" of container 10 by a lock ring 40" having a ring housing 41 for ring magnet 80, and configured to engage with container 10 at end portion 10", for example, by a screw-threaded coupling, not shown, or by a click engagement as shown in FIGS. 4-6. In this case, end portion 10" has alternate radially compliant longitudinal elements 14 that defines longitudinal channels 13 and have inward radial projections 14' configured to receive and lock ring 40" within container 10 in a click engagement. Also first end 71 of spring 70 can be fastened to container 10 by a lock ring, for example by same ring 40", which has in this case a ring housing 42 for receiving spring 70.

With reference to FIGS. 7-9, an artificial endourethral sphincter 102 is described according to a second modification of the first exemplary embodiment, also comprising a valve unit 20 including a stopper 26 slidably arranged within container 10, to which preferably ring-shaped actuation magnet 66 is connected, and that has a stopper abutment element 27 configured to fluid-tightly engage with a housing or sealing element 28' machined in an inner wall of container 10 or in a ring 40' arranged therein, in order to provide block configuration B when actuation magnet 66 and stopper 26 are in position dB (FIG. 3B) corresponding to the block configuration of valve unit 20 (FIGS. 7 and 8).

Artificial sphincter 102 has two passageways 43',43" within container 10 and slidable stopper 26, respectively, communicating with each other via a first passage port 44' made through a side surface, in this case cylindrical, of slidable stopper 26. The latter has an end opposite to abutment element 27 providing a second passage port 44" that communicates with an opening 45 of container end 10'". This allows a flow of urine 5 along a path that is formed when stopper 26 is in position $d_R$ (FIG. 3D), which corresponds to the release configuration of valve unit 20 (FIG. 9).

Figure 10:
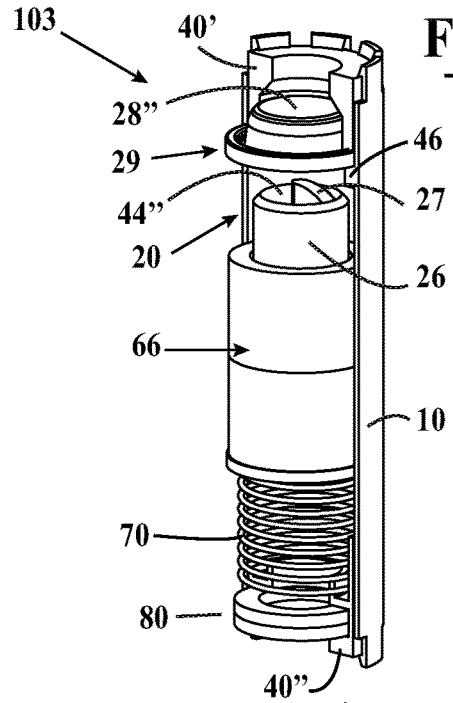
FIG. 10 is a perspective view of an artificial endourethral sphincter, in which a portion of the container is removed, according to a third modification of the first exemplary embodiment, in which a slidable stopper and a sealing housing made as a removable valve element are provided.
Figure 11:
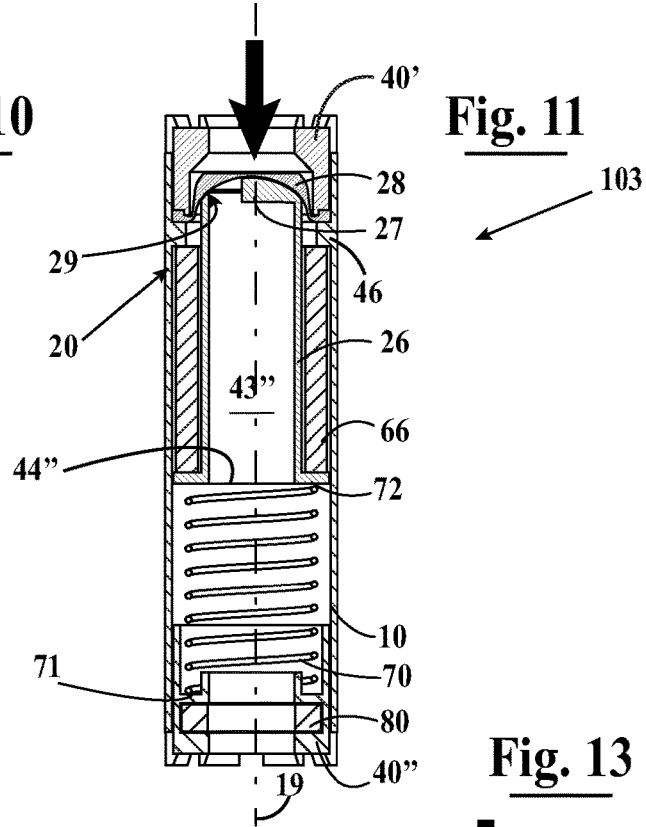
FIG. 11 is a cross sectional view of the artificial sphincter of FIG. 10, in a block configuration.

With reference to FIGS. 10-13, an artificial endourethral sphincter 103 is described according to a third modification of the first exemplary embodiment, also comprising a valve unit 20 including a stopper 26 slidably arranged within container 10, to which preferably ring-shaped actuation magnet 66 is connected. Stopper 26 has a stopper abutment element 27 configured to fluid-tightly engage with a sealing housing 28" made in a valve element 29, so as to provide block configuration B when actuation magnet 66 and stopper 26 are in position dB (FIG. 3B) corresponding to the block configuration of valve unit 20 (FIG. 11).

Figure 14:
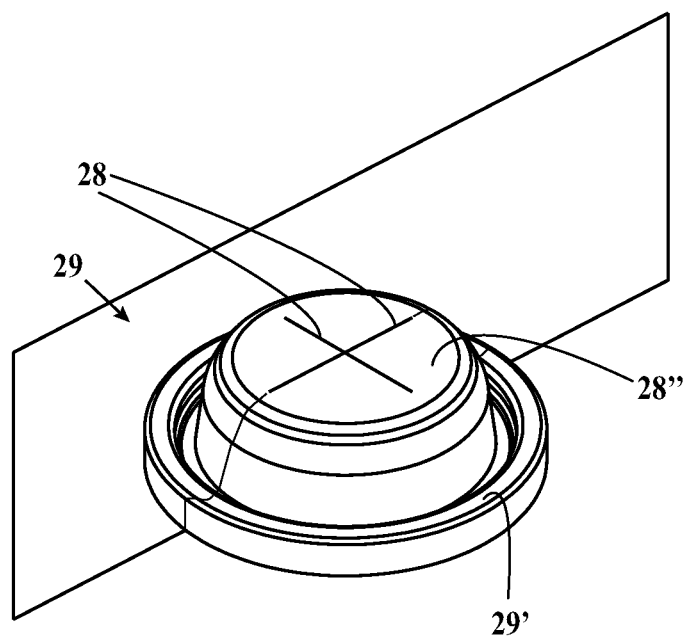
FIGS. 14 and 15 are a perspective view and a cross sectional view, respectively, of a valve element comprising a shell portion of the artificial sphincter of FIGS. 10-13.
Figure 15:
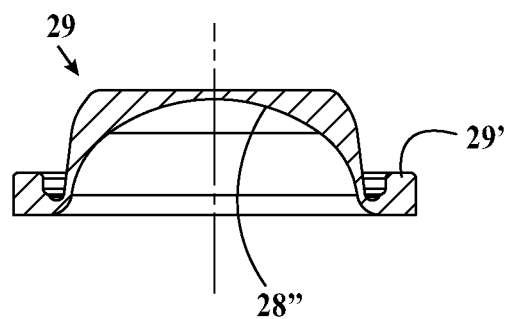

Valve element 29, as shown in FIGS. 14 and 15, comprises a resilient shell portion 28'", which forms the sealing housing of valve unit 20, and comprises an ring edge 29' for montage within container 10, for example by arranging the valve element on a ring inner projection 46 of container 10 and by locking it by ring 40', the ring edge arranged between ring projection 46 and ring 40'.

The resilient shell portion has a through notch 28, preferably a plurality of through notches 28 converging towards one region of shell portion 28" preferably a top or central region thereof. Shell portion 28" is shown in FIGS. 14 and 15 in a closed configuration, in which the edges of through notch or notches 28 are adjacent to each other and provide a seal against a urine pressure P lower than a critical value P*, so as to maintain a convex shape of shell portion 28" opposite to slidable stopper 26. When the critical pressure P* is exceeded, resilient shell portion 28" collapses reversibly into a concave shape (FIG. 13) opposite to the convex shape, and an open configuration is obtained, in which through notch or through notches 28 is/are open and allow(s) the liquid to flow.

Figure 12:
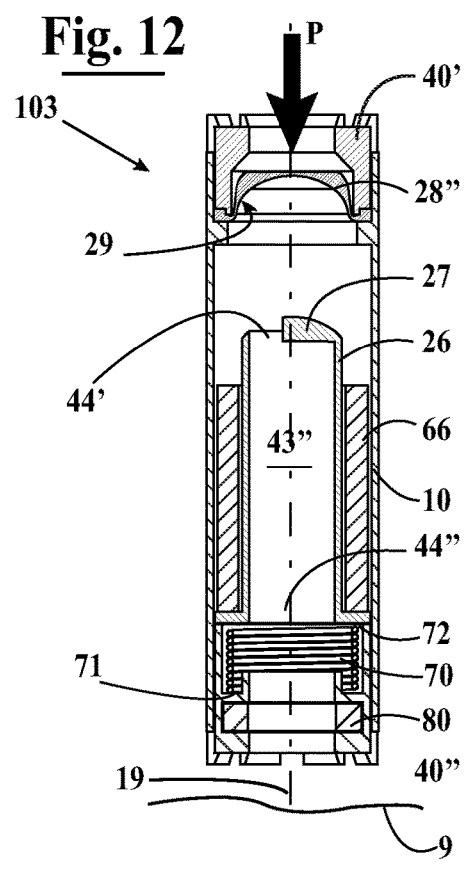
FIGS. 12 and 13 are cross sectional views of the artificial sphincter of FIG. 10 in a release configuration, with a shell portion of the valve element respectively in a closed configuration and in an open configuration.
Figure 13:
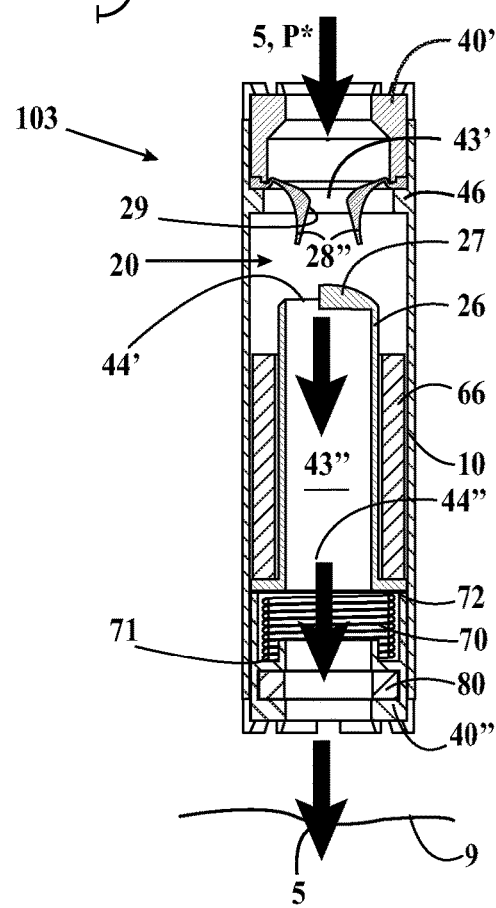

Artificial sphincter 103 and slidable stopper 26 have passageways and passage ports 43',43",44',44",45 configured to define a path, similarly to artificial sphincter 102 of the second modification, when stopper 26 is in position $d_R$ (FIG. 3D) corresponding to the release configuration (FIGS. 12 and 13). However, in this case the release configuration (FIG. 13) is obtained when upper resilient shell portion 28" takes its own open configuration, due to an intra-bladder pressure P* or higher.

With reference to FIGS. 16A to 20, an artificial endourethral sphincter 104 is described according to a fourth modification of the first exemplary embodiment. Container 10 is shown in a perspective cross sectional view, in which only a semicylindrical half thereof is shown (FIG. 16B). In this sphincter, the valve unit comprises a torsionally compliant tubular body 20 in which a torsionally compliant central portion 22 is arranged about its own longitudinal axis 29 and between first and a second end portions 21,23, in particular between end portions equal to each other, whereas first and second end portions 21,23 are torsionally stiffer than central portion 22. For instance, central portion 22 can be a cylindrical portion, in particular it can have a substantially circular cross section. Central portion 22 inside is arranged to change its configuration by a given torsion 8,9", i.e. by a differential rotation of end portions 21,23 about axis 29, from a configuration in which a passageway 24 is provided, which corresponds to the release configuration of valve unit 20, to a configuration in which the inner walls are in contact with one another and completely block passageway 24 in at least one part of central portion 22, so as to prevent any liquid flow, or vice-versa.

First end portion 21 is integrally connected to container 10, by means of its upper end portion 21, in particular the latter is arranged between ring inner projection 46 of container 10 and lock ring 40' in the same way as the valve element of sphincter 103, so as to prevent both tubular body 20 from translating within container 10 and upper end portion 21 from turning about axis 19 of container 10, which coincides with axis 29 of tubular body 20.

In the modification of FIGS. 18 and 20, torsionally compliant tubular body 20 has three radially arranged longitudinal walls 25, typically at 120° from each other, which divide passageway 24 into three independent channels.

Translation movement 67',67" of actuation magnet 66 causes rotatable actuation cylinder 30 to perform rotation movement 68',68". To this purpose, an actuation unit 60 is provided within container 10. The actuation unit comprises a fixed hollow cylindrical guide element 50 that has a channelled part 55 providing a first channel 56 and a helical portion 51 thereof, and also comprises a rotatable actuation cylinder 30 that has an end part 31 integral to second end portion 23 of torsionally compliant tubular body 20 and a channelled part 35 providing a linear second channel 36 telescopically arranged outside of guide element 50, at the same height as first channel 56. To this purpose, rotatable actuation cylinder 30 internally provides a housing 37 configured to rotatably and slidably receive channelled part 55 of guide element 50.

Actuation unit 60 also comprises a support 61 supporting fixed actuation magnet 66, in this case an annular actuation magnet. Support 61 can comprise longitudinal flexible portions 64 providing outwards protruding lock teeth 64', so that magnet 66 can be mounted to support 61 by a click engagement.

Guide element 50 can be connected to container 10 by outwards protruding lock teeth 53, configured to engage with lock channels 13 provided at end 10" of container 10.

As shown in FIGS. 17 and 19, lower end portion 23 of tubular body 20 can be fixed to actuation cylinder 30 by tightening it between a ring inner projection of actuation cylinder 30 and a lower lock ring. Preferably, as described above, the channelled part 35 of rotatable actuation cylinder 30 comprises longitudinal flexible portions 33 (FIG. 16A), in order to assist the installation of a lower lock ring 37' within rotatable actuation cylinder 30. In order to increase the flexibility of longitudinal portions 33, the longitudinal linear second channels 36 can have circumferential extensions 34, at the end opposite to the free end of longitudinal portions 33.

In order to perform rotation movement 68',68" of rotatable actuation cylinder 30, at least one but preferably a plurality of external protrusions 62 radially extend from support 61, said protrusions engaging with both first and second channels 56,36 of fixed guide cylindrical element 50 and of rotatable actuation cylinder 30.

For instance, this protrusion can comprise a pin 62 housed within a radial hole 63 of a portion 65 of support 61, such as an engagement portion 65 with rotatable actuation cylinder 30.

Since guide element 50 is integrally connected to container 10, when slidable magnetic actuation unit 60 translates along hollow container body 10, is forced to rotate about its axis 19 and, engaging with the second channel 36 by pin 62, and forces rotatable actuation cylinder 30 to perform rotation movement 68',68" about axis 19, thus causing also second end portion 23 of torsionally compliant tubular body 20 to rotate. Since upper portion 21 of tubular body 20 cannot rotate about its axis 29, as explained above, rotation 68',68" of rotatable actuation cylinder 30 causes torsion 8,9 of tubular body 20.

With the above-described arrangement, a translation movement 67',67" of actuation magnet 66, in this case integrally to support 61, causes outer radial protrusion or pin 62 to move from a first extreme position 51' to a second position 51" of helical part 51 of channel 56, and vice-versa, respectively, causing tubular body 20 to twist and to move from block configuration B (FIGS. 17,18) to release configuration R (FIGS. 19,20) and vice-versa, respectively.

Advantageously, first channel 56 comprises a linear longitudinal portion 52, i.e. a portion oriented in the same way as the axis of cylindrical guide element 50, said portion adjacent to extreme position 51' corresponding to block configuration B. As long as protrusion 62 is in the linear longitudinal end portion 52, opening translation movement 67" of slidable magnetic actuation unit 60, cannot cause any rotation of rotatable actuation cylinder 30, therefore tubular body 20 remains in block configuration B. This is useful to prevent the unintentional opening of tubular valve body 20.

Such an event could happen if tubular body 20 is made of a resilient material, in which case tubular body 20 would be prone to return from block configuration B to release configuration R, which is normally a rest configuration in which tubular body 20 is manufactured, and corresponds to the open configuration, therefore inner elastic stresses arise in the deformed closed configuration, which tend to recall the tubular body to the open rest configuration. Moreover, an unintentional opening could occur in the case of a sudden movement of the subject who bears the sphincter, such as jumps, vehicle jerks, fast stair climbing, and the like.

In artificial sphincters 102, 103, 104 of the second, third and fourth modifications, stabilization magnet 80 and spring 70 can be mounted by a lock ring 40" of the type described with reference to artificial sphincter 101 of the first exemplary modification. Ring 40' can be fixed at end 10' of container 10 by coupling means similar to those described for ring 40" and end portion 10".

With reference to FIGS. 40-45, an endourethral artificial sphincter 105 is described similar to artificial sphincter 103 of FIG. 10, from which differs in that it comprises a manoeuvre electromagnet 91 housed within container 10. In this modification, the electromagnet has the shape of a winding 91 of coils of an electrically conductive material arranged in a plane π perpendicular to longitudinal axis 19. In this way, not limitative, electromagnet 91 is electrically fed by a control unit 95, and can form a manoeuvre magnetic field whose magnetic axis 99, indicated as the manoeuvre magnetic axis, is substantially parallel to longitudinal axis 19.

In the case of winding 91 of coils 92, control unit 95 is configured to supply an electric current to manoeuvre electromagnet 91. The current can have one out of two possible directions, so that the manoeuvre magnetic axis is oriented in the same way as second magnetic axis 69 of actuation magnet 66 (FIG. 45) or in a way opposite to it (FIG. 42). This way, actuation magnet 66, and then slider 26, receives a manoeuvre magnetic force $F_M'$,$F_M''$ that has the same direction or the direction opposite, respectively, with respect to stabilization magnetic force $F_m$ and, accordingly, the opposite direction or the same direction, respectively, with respect to resilient force $F_e$, therefore the manoeuvre magnetic force is directed towards one or another end portion 10',10", respectively, of container 10.

Control unit 95 is also configured to generate said current with such an intensity that manoeuvre magnetic force $F_M'$, $F_M''$ having the first or the second direction can cause slider 26 to move from the current advanced position to the retracted position, provided that it is higher than the resultant of resilient force $F_e$ and of stabilization magnetic force $F_m$, which are directed towards the retracted position and towards the advanced portion, in the two cases, respectively. In other words, electromagnet 91 plays the role of manoeuvre magnet 90 of FIG. 3A.

More in detail, in order to move the endourethral sphincter 105 from the block configuration (FIG. 41) to the release configuration (FIG. 43), a remote control 96 is used (FIG. 42) to send an opening wireless signal 97 to control unit 95, so as to actuate a program means resident in control unit 95 for electrically feeding manoeuvre electromagnet 91. This way, a magnetic field in is generated whose magnetic induction vector is arranged to repel slider 26 along with actuation magnet 66. Once the release configuration of FIG. 43 has been obtained, as described above for artificial sphincter 103 of the third modification (FIGS. 10-13), the patient can increase the abdominal pressure to cause resilient shell portion 28" to reversibly collapse into the concave shape (FIG. 44), thus obtaining an open configuration, in which valve element 29 is open and allows the flow of urine 5.

Similarly, in order to move the endourethral sphincter 105 from the release configuration of FIG. 44 back to the block configuration of FIG. 41, remote control 96 is used again, to send a closing wireless signal 97 to control unit 95, so as to actuate the program means of control unit 95 for feeding manoeuvre electromagnet 91 in such a way to generate a magnetic field whose magnetic induction vector is arranged, this time, to attract slider 26 along with actuation magnet 66, to bring it back to the block configuration.

Even if the figures only show the electromagnet of endourethral sphincter 103 of the third modification, it can be introduced into any endourethral or extraurethral artificial sphincter of the first exemplary embodiment that has slidable actuation magnet 66.

Second Exemplary Embodiment

Figures 21A, 21B, 21C, 21D, 21E, 21F, 21G, 21H:
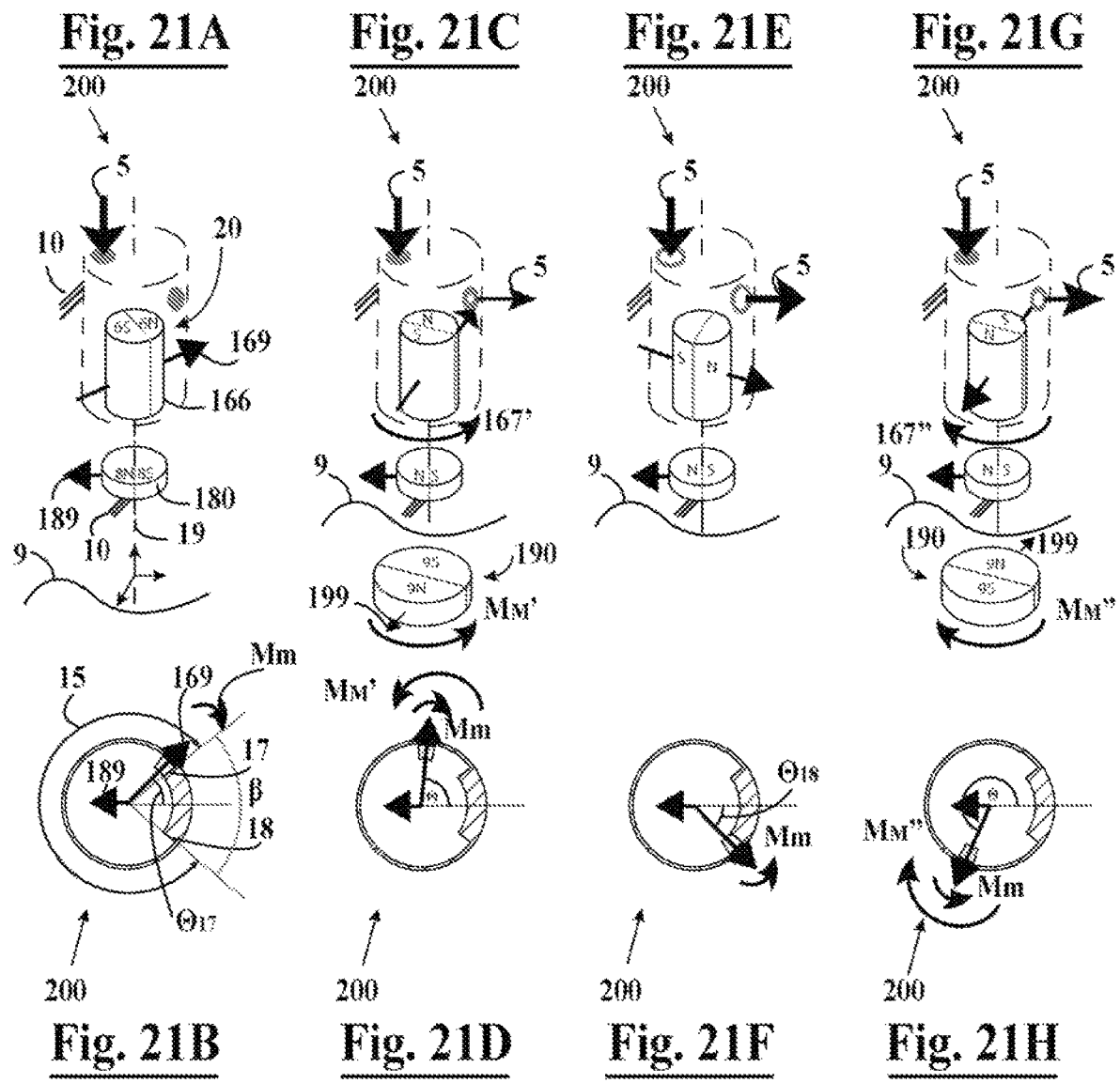
FIGS. 21A-21H are a perspective view and a cross sectional view diagrammatically showing an artificial sphincter according to a second exemplary embodiment of the invention, in subsequent steps of an opening-closing cycle, FIG. 21I diagrammatically show the moments that act on an actuator of the sphincter of FIGS. 21A-21H.

As diagrammatically shown in FIG. 21A, in a second exemplary embodiment, artificial sphincter 200,220 comprises a container 10 configured to be connected to urethra 4 (FIG. 1), in which valve unit 20 is arranged. The valve unit is configured to move from release configuration R to block configuration B, and vice-versa. Container 10 also encloses a fixed stabilization magnet 180 and an actuation magnet 166 rotatably arranged about axis 19 of container 10, with respective magnetic axes 189 and 169 arranged transversally, in particular perpendicularly, with respect to longitudinal axis 19 of container 10. In the present exemplary embodiment, actuation magnet 166 and stabilization magnet 180 are cylindrical magnets, with the poles 6N,6S and 8N,8S, respectively, arranged along an own diameter, in other words actuation magnet 166 and stabilization magnet 180 are radial magnets. Stabilization magnet 180 has an own reference pole 8N in an angular reference position $E_2$ within an actuation angular sector 15 defined between a first angular position $S_{17}$ and a second angular position $S_{18}$ with respect to container 10, and therefore subtended by an actuation angle α of amplitude $2\pi-\theta_{17}-\theta_{18}$, whereas actuation magnet 166 is a rotatable magnet with an own actuation pole 6N, which has the same name as the reference pole, arranged between the first and the second angular positions $S_{17}$,$S_{18}$, within actuation angular sector 15. On the other hand, a movement limitation 17,18 prevents actuation magnet 166 from rotating with actuation pole 6N located within the sector 15' subtended by angle β, wherein the latter and actuation angle α are explementary angles, and β has therefore amplitude $\theta_{17}+\theta_{18}$.

With such an arrangement, stabilization magnet 180 produces on actuation magnet 166 a magnetic moment $M_m$ that depends upon the orientation γ of actuation magnet 166 about longitudinal axis 19. This relationship is shown in the diagram also shown in FIG. 21I.

Point $E_2$, corresponding to the orientation γ=π, where magnetic axes 169 and 189 are oriented in the same way, is an instable equilibrium position of magnet 166 with respect to magnet 180. In fact, any rotation towards position $S_{17}$ or $S_{18}$, causes magnetic axis 169 to have an orientation in which actuation magnet 166 receives a positive or negative magnetic moment $M_m$, respectively, which moves it further away from actual position $E_2$ and brings it respectively towards the positions $S_{18}$ and $S_{17}$.

Actuation magnet 166 is connected to valve unit 20, directly or by a mechanism, in such a way that a rotation 167',167" of actuation magnet 166 from angular position $S_{17}$ or starting from angular position $S_{18}$, or vice-versa, causes valve unit 20 to move from release configuration R to block configuration B.

With reference to FIGS. 21A-21H, the operation of artificial sphincter 200,220 will now be described. FIG. 21A shows sphincter 200,220 in block configuration B, where actuation magnet 166, connected to valve unit 20, is in position $S_{17}$, i.e. it has its magnetic axis oriented to $180-\theta_{17}$ with respect to magnetic axis 189 of stabilization magnet 180, and stabilization magnetic moment $M_m$ that stabilization magnet 180 produces on actuation magnet 166 is negative and therefore maintains valve unit 20 in the block configuration.

Figure 21I:
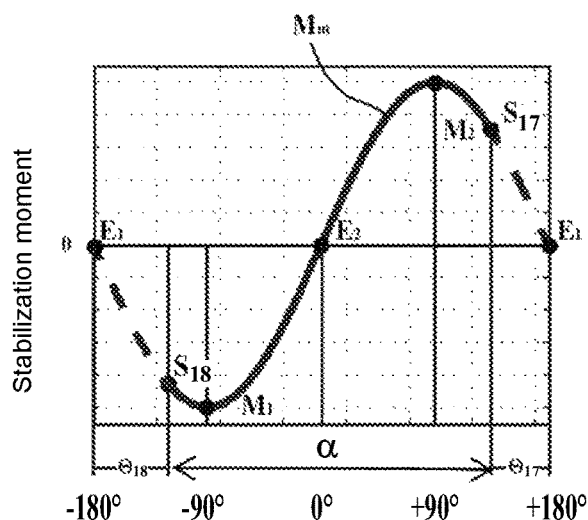
Figure 22B:
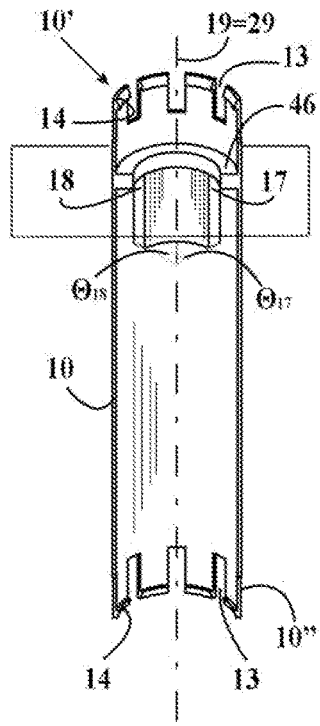
FIGS. 22A and 22B are exploded perspective views of an artificial endourethral sphincter in a first modification of the second exemplary embodiment, in which a torsionally compliant stopper is provided.
Figure 22A:
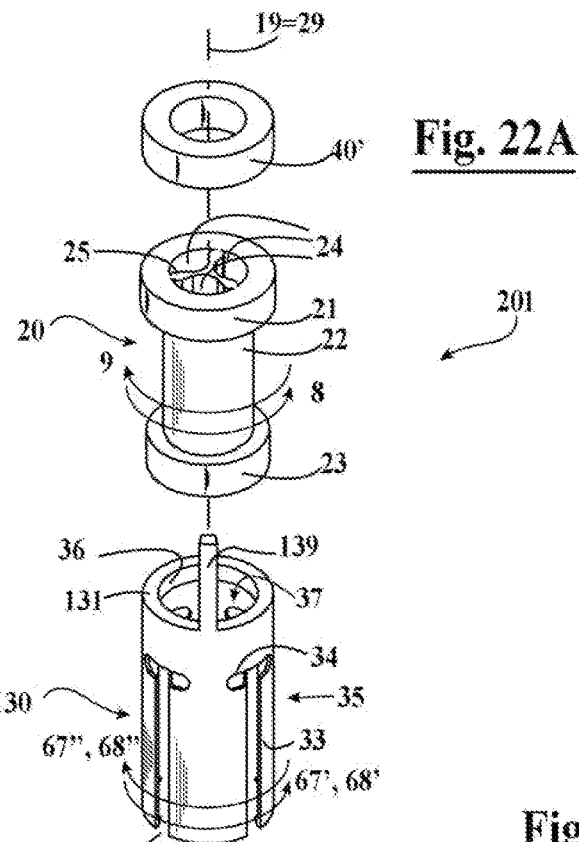

As shown in FIG. 21C, in order to bring valve unit 20 to release position R, a manoeuvre magnet 190 is positioned with its own magnetic axis 199 transversally arranged with respect to axis 19, preferably orthogonal thereto, and is oriented so as to exert a positive manoeuvre magnetic moment $M_M'$, i.e. opposite to stabilization moment $M_m$, on actuation magnet 166. The features of manoeuvre magnet 190 and its position to cause extraurethral sphincter 200 to open are selected in such a way that the overall moment acting on actuation magnet 166, i.e. the resultant of moments $M_M', M_m$ exerted on actuation magnet 166 by manoeuvre magnet 190 and by stabilization magnet 180 is positive, i.e. counterclockwise-oriented, according to the sign convention used herein. This way, actuation magnet 166 performs a positive, i.e. counterclockwise, rotation, and causes valve element 20 to move away from block condition B. As also shown in the diagrammatical view of FIG. 21D, manoeuvre magnet 190 can be progressively rotated counterclockwise, in order to cause actuation magnet 166 to perform a rotation 167' at least until actuation pole 6N has passed through position $E_2$, as also shown in the diagram of FIG. 21I, i.e. it has attained a position in which stabilization magnetic moment $M_m$ exerted on rotatable actuation magnet 166 by a stabilization magnet 180 alone can bring rotatable actuation magnet 166 to position $S_{18}$. Therefore, as shown in FIGS. 21E-21F, even if manoeuvre magnet 190 is removed, i.e. is moved away indefinitely from extraurethral sphincter 200, 220, rotatable actuation magnet 166 moves back and remains in position $S_{18}$, and valve unit 20 reaches and remains in release configuration R.

As view 21G diagrammatically shows, manoeuvre magnet 190 is positioned again and preferably rotated to returning artificial sphincter 200 to the block configuration, but this time with an initial orientation of magnetic axis 199 and with a clockwise rotation direction, such that a new manoeuvre magnetic moment $M_M''$ is negative, i.e. still opposite to stabilization moment $M_m$, in order to cause actuation magnet 166 to perform a rotation 167'' at least until actuation pole 6N has passed through position $E_2$, i.e. it has a position in which the stabilization magnetic moment $M_m$ exerted on rotatable actuation magnet 166 by stabilization magnet 180 alone can bring rotatable actuation magnet 166 to position $S_{17}$. Therefore, even if manoeuvre magnet 190 is removed, i.e. is moved away indefinitely from extraurethral sphincter 200,220, rotatable actuation magnet 166 moves back and remains in position $S_{17}$, and valve unit 20 reaches and remains in block configuration B (FIGS. 21A,21B).

With reference to FIGS. 22A to 27, an artificial endourethral sphincter 201 is described according to a first modification of the second exemplary embodiment, in which the valve unit comprises a torsionally compliant tubular body 20 constructed and connected to container 10 in the same way as artificial endourethral sphincter 104 of the first exemplary embodiment.

Container 10 encloses an actuation cylinder 130 rotatably arranged about its own axis 19 and connected to second end portion 23 of torsionally compliant tubular body 20, in such a way that a rotation of actuation cylinder 130 about axis 19 causes a torsional deformation 8,9 of torsionally compliant tubular body 20. Moreover, actuation magnet 166 is integrally mounted to rotatable actuation cylinder 130 with an own actuation pole, for example North pole 6N, in a predetermined angular position with respect to cylinder 130.

In order to cause actuation magnet 166 to rotate while maintaining actuation pole 6N within actuation sector 15, set between angle $\pi-\theta_{17}$ and angle $-(\pi-\theta_{18})$, actuation cylinder 130 comprises a projection, in particular an axial projection, i.e. an abutment member 139 protruding from a peripheral portion 131, at a predetermined abutment angle $\gamma$ from actuation pole 6N, in this case $\gamma=0$, i.e. actuation magnet 166 is arranged with actuation pole 6N at abutment member 139. On the other hand, container 10 has inner protrusions, i.e. abutment elements 17,18 at the two angular positions $S_{17}$ and $S_{18}$, large enough to abut against abutment member 139 by a rotation of actuation cylinder 130, and to prevent actuation cylinder 130 from rotating with actuation magnet 6N out of actuation sector 15. In other words, the abutment elements 17 and 18, which can be the faces of a same projection radial inner of container 10, defining the constraint kinematic above mentioned.

Figure 26:
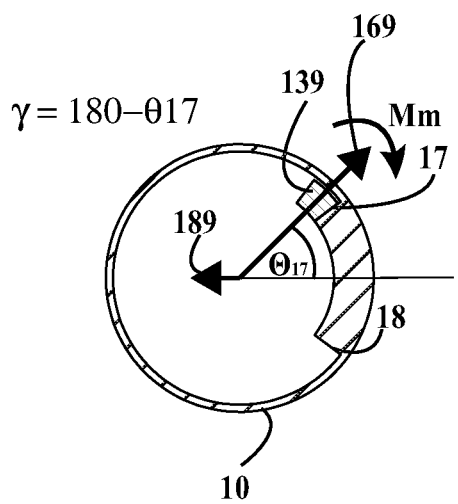
FIGS. 26 and 27 are cross sectional views as in FIG. 23, in the configurations of FIGS. 22A and 22B, respectively.
Figure 25:
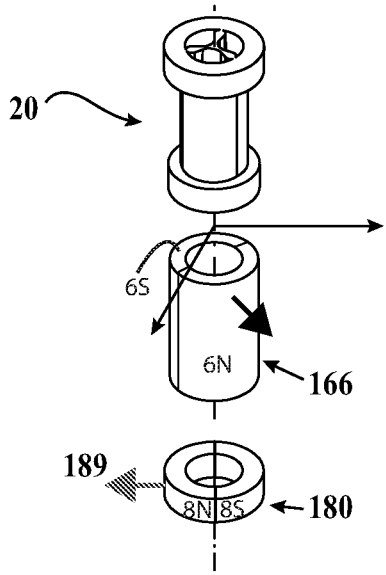
Figure 27:
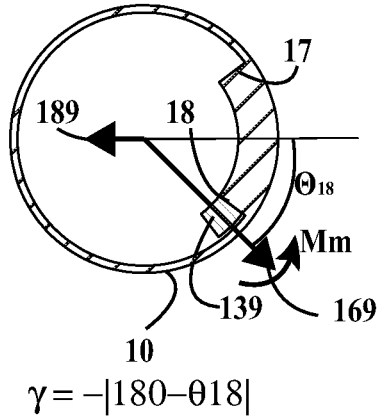
Figure 28:
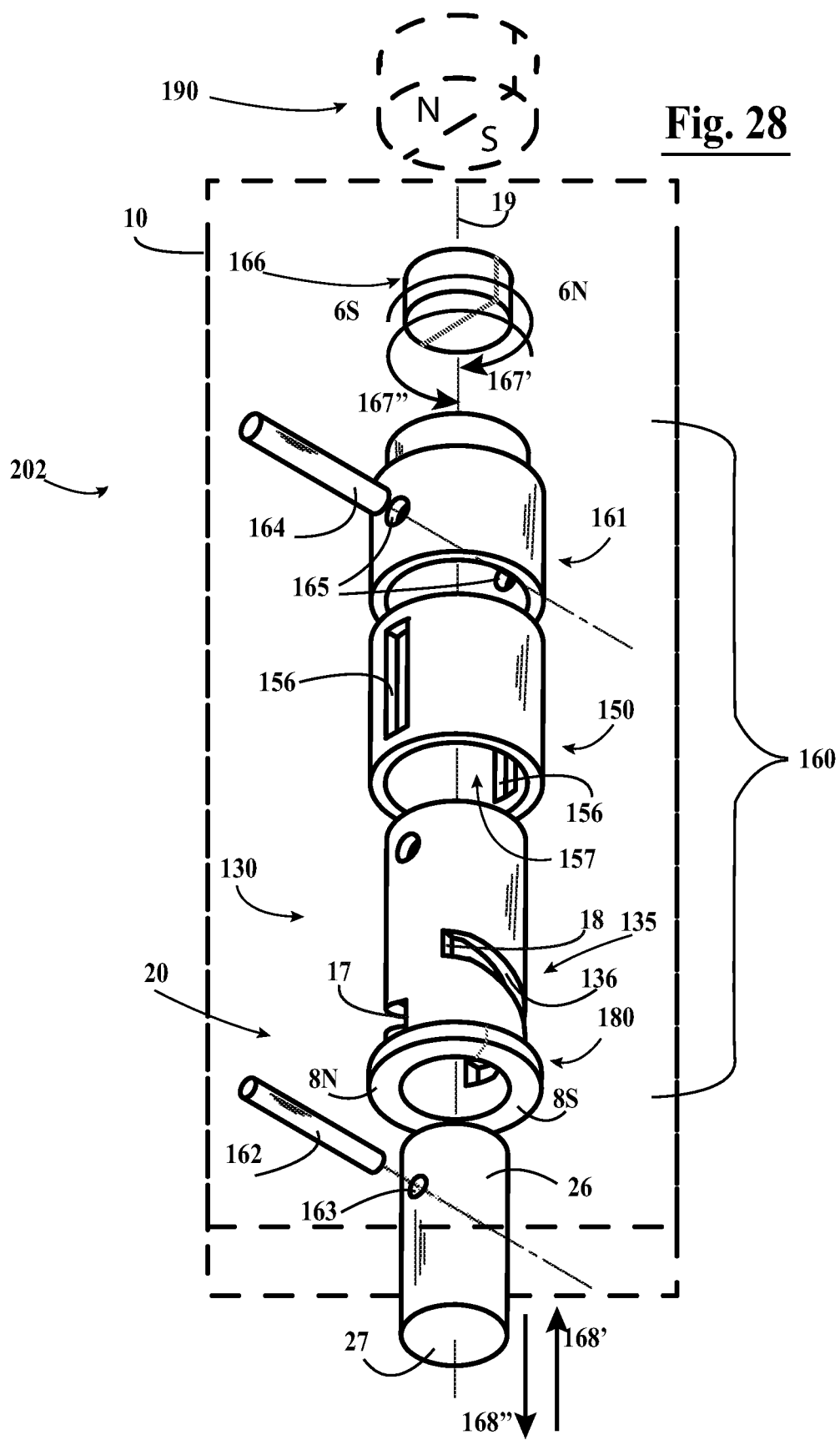
FIG. 28 is an exploded perspective view of an artificial sphincter in a second modification of the second exemplary embodiment of the invention.
Figure 29:
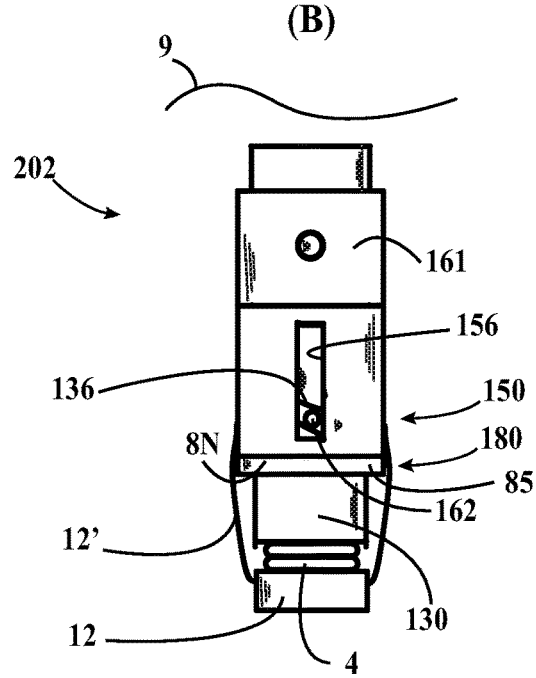
FIGS. 29 and 30 are partial cross sectional views of an artificial extraurethral sphincter according to FIG. 28, in a block configuration and in a release configuration, respectively.

The unit comprising tubular body 20, rotatable actuation cylinder 130 and actuation magnet 166 is mounted to container 10 in such a way that, when abutment member 139 abuts against one of the abutment elements 17,18, in this case against abutment element 18 as shown in FIG. 27, tubular body 20 is in the release configuration, whereas, when abutment member 139 abuts against the other abutment element, in this case against abutment element 17 as shown in FIG. 26, tubular body 20 is in the block configuration. By another point of view, angles $\theta_{17}$ and $\theta_{18}$ are selected so that angle $\alpha=2\pi-\theta_{17}-\theta_{18}$ subtending actuation sector 15 is wide enough to bring tubular body 20 from the release configuration of FIG. 25, in particular an undeformed open tubular configuration, to the block configuration of FIG. 24, in particular, without excessively stressing second end portion 23 when in the block configuration.

Figure 23:
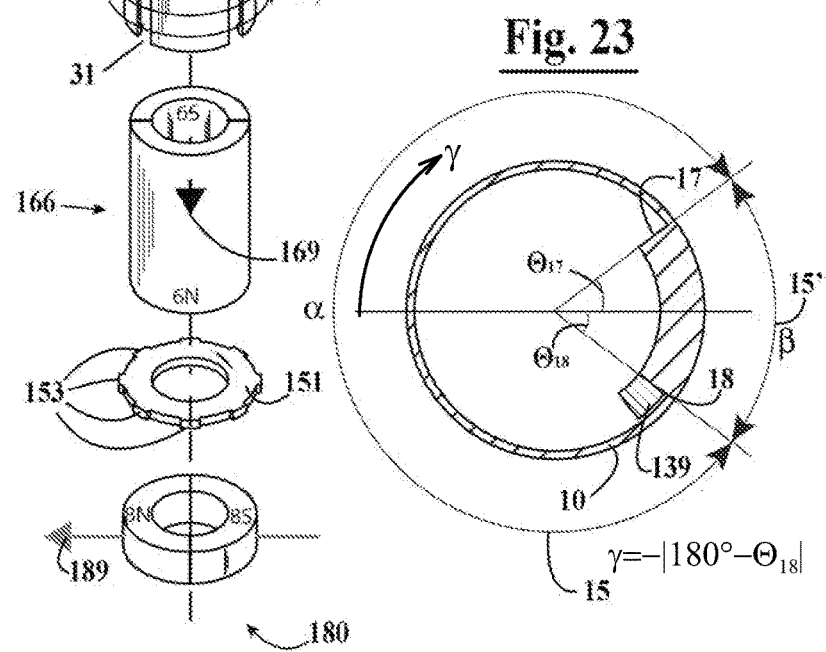
FIG. 23 is a cross sectional view of the sphincter shown in FIGS. 22A and 22B, made at abutment elements of the container.
Figure 24:
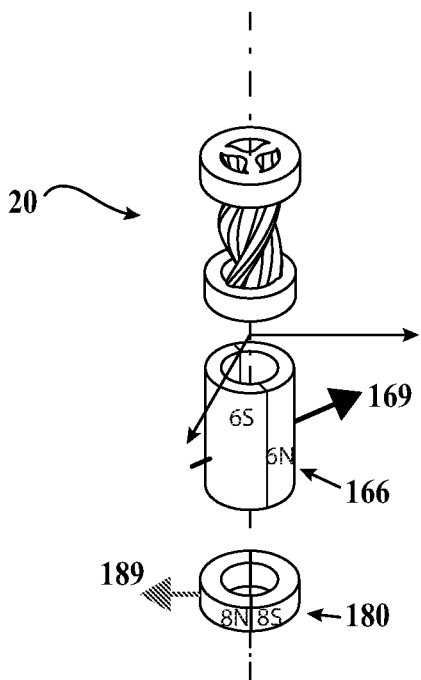
FIGS. 24 and 25 show the relative positions of a stabilization magnet and of an actuation magnet of the sphincter of FIGS. 22A and 22B, in a block configuration and in a release configuration, respectively.

The primary stabilization magnet 180 is arranged at end 10" of container 10, and has its reference pole, in this case North pole 8N, in a predetermined angular position within actuation sector 15, in particular at the centre of the sector and, for example, at the position where $\gamma=0$ according to the reference of FIG. 23.

Stabilization magnet 180 can be connected to container 10 in the same way as stabilization magnet 80 of artificial sphincter 104 of FIG. 16A, with or without a lock ring 40", by means of inward radial projections 14' of longitudinal elements 13, configured to receive and to lock stabilization magnet 80 or lock ring 40" within container 10 in a click engagement. Moreover, in order to arrange actuation cylinder 130 at a suitable distance from stabilization magnet 180, a ring spacer 151 can be provided with radially protruding lock teeth 153, configured to engage with lock channels 13 at end 10" of container 10.

With reference to FIGS. 28-32, an artificial extraurethral sphincter 202 is described according to a second modification of the second exemplary embodiment, also comprising, as artificial sphincter 101, a container 10 that comprises a cover 12 (FIGS. 4,29,30) and a valve unit 20 including a stopper 26 slidably arranged within container 10 for tightening a segment of urethra 4, and for allowing a dilation thereof, in a block configuration B (FIG. 29) and in a release configuration R (FIG. 30), respectively.

Rotation 167',167" of actuation magnet 166 causes slidable stopper 26 to perform a translation movement 168',168" between locking position B and release position R, and vice-versa. To this purpose, an actuation unit 160 is provided within container 10. The actuation unit comprises a fixed hollow cylindrical guide element 150 that has a linear channel 156 parallel to longitudinal axis 19 and arranged at a predetermined angular distance, preferably about zero, from reference pole 8N of stabilization magnet 180, and also comprises a rotatable actuation cylinder 130 with a channelled part 135 providing a helical channel 136 and rotatably arranged within guide element 150, at the same height as linear channel 156. To this purpose, guide element 150 internally provides a housing 157 configured to rotatably receive channelled part 135 of rotatable actuation cylinder 130.

Actuation unit 160 also comprises a support 161 rotatably arranged within container 10 and integrally connected to actuation cylinder 130. Actuation magnet 166, in this case a disc-shaped magnet, is rigidly connected to support 161, for example by a pin 164 engaging with two holes 165 of support 161.

In order to obtain translation movement 168',168", at least one external protrusion 162 extends radially to stopper 26 and engages with both helical channel 136 of rotatable actuation cylinder 130, and linear channel 156 of guide element 150. For example, the external protrusion is a pin 162 that can be housed within a radial hole 163 of stopper 26.

Since guide element 150 is integrally connected to container 10, when actuation magnet 166 rotates about its axis 19 along with support 161 and so also along with rotatable actuation cylinder 130, stopper 26 is forced to translate along axis 19.

Figure 30:
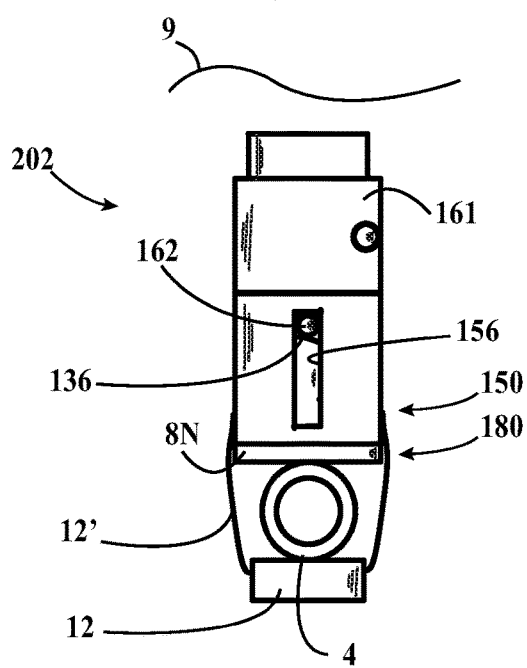
Figure 31:
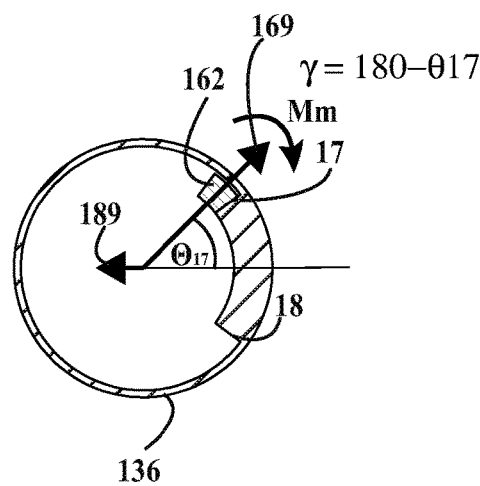
FIGS. 31 and 32 are cross sectional views of the sphincter of FIGS. 29 and 30, in the respective configurations of the sphincter, made at abutment end portions of a helical channel of a guide element.
Figure 32:
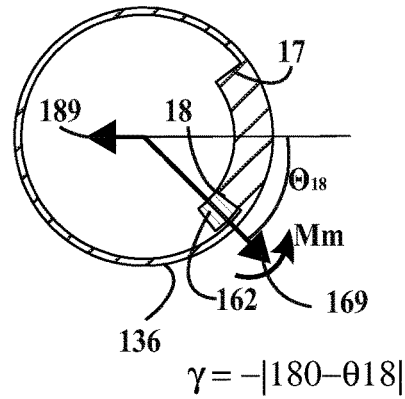
Figure 46:
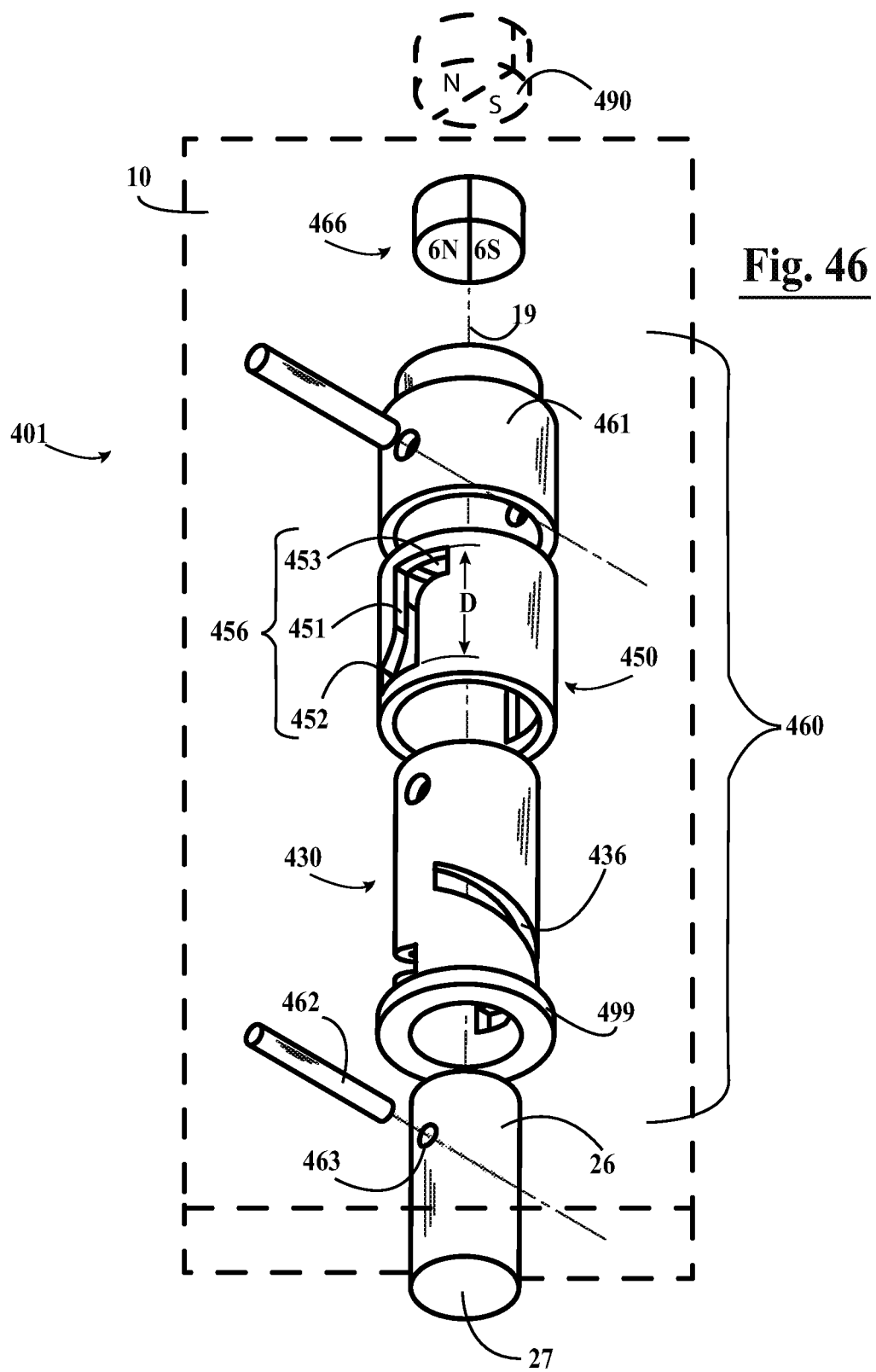
FIG. 46 is an exploded perspective view of an artificial extraurethral sphincter in a fourth exemplary embodiment of the invention.
Figure 47:
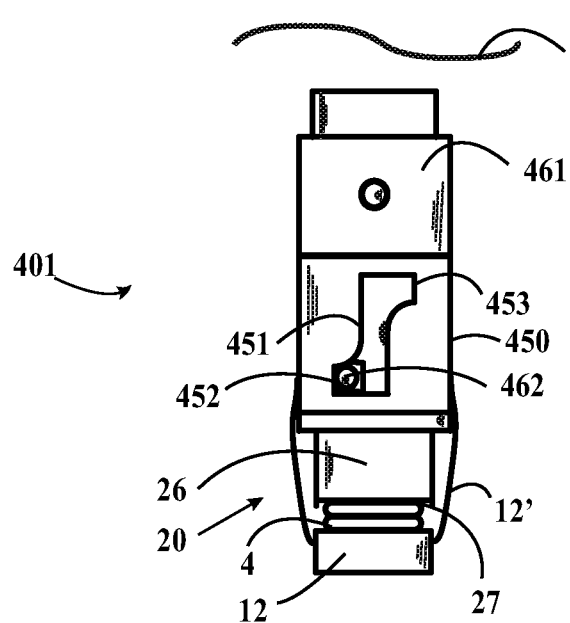
FIGS. 47-50 are side views of the sphincter of FIG. 46, in subsequent steps of an opening-closing cycle.

This way, when actuation pole 6N is located in angular position $S_{17}$ or in angular position $S_{18}$ (FIGS. 31 and 32, respectively) stopper 26 is respectively in a more extended position and in a more retracted position, as in the figures, or vice-versa, with respect to rotatable actuation cylinder 130 and guide element 150, and valve unit 20 is in the block configuration (FIG. 29) and in the release configuration (FIG. 30), respectively. In the first case, stopper abutment element 27 of stopper 26 engages with cover 12 compressing and closing segment of urethra 4 (FIG. 29), whereas, in the latter case, it is at a distance therefrom to allow segment of urethra 4 to have an open configuration (FIG. 30).

In order to cause actuation magnet 166 to rotate while maintaining actuation pole 6N always within actuation sector 15, i.e. between angle $\pi-\theta_{17}$ and angle $-(\pi-\theta_{18})$, helical channel 136 has an angular amplitude, between the surfaces of abutment ends 17 and 18, equal to the amplitude $2\pi-\theta_{17}-\theta_{18}$ of angle $\alpha$ subtended to actuation angular sector 15 (FIG. 21I), and actuation magnet 166 is mounted to support 161 with actuation pole 6N within the sector defined by two abutment surfaces 17 and 18, in particular at the centre of this sector.

Third Exemplary Embodiment

With reference to FIGS. 33A to 39, an artificial endourethral sphincter 301 is described according to a fourth exemplary embodiment, in which the valve unit comprises a torsionally compliant tubular body 20 structured and connected to container 10 in the same way as artificial sphincters 104 and 201 of the first and of the second exemplary embodiment, respectively.

In order to operate sphincter 301, i.e. to cause torsionally compliant tubular body 20 to move from block configuration B (FIG. 37) to release configuration R (FIG. 39), and vice-versa, by a rotation of second end portion 23, a motor 360 is provided comprising a stator 350 coaxially and integrally mounted to container 10, and also comprising a rotor 351 rotatably arranged within stator 350. As shown in FIGS. 34-36, rotor 351 comprises an actuation magnet 366 with a reference pole 6N, in this case the North pole, facing an inner surface of stator 350. More in detail, rotor 351 can comprise an end ring portion 352 having a cylindrical cross section and configured to be fixedly connected to actuation cylinder 330. Rotor 351 also comprises a support diameter portion 354 of actuation magnet 366 arranged along a diameter within end ring portion 352, and equipped with an extension along the axis of stator 350.

Stator 350 comprises two stabilization magnets 381,382 angularly spaced apart from each other by a predetermined actuation angle $\gamma$ having a vertex on longitudinal axis 19. Each stabilization magnet 381,382 has an own actuation pole 8S, of name opposite to reference pole 6N of actuation magnet 366, in this case the South pole, oriented inwards of stator 350, and the other pole 8N oriented outwards of stator 350. Stator 350 also comprises a plurality of manoeuvre electromagnets 391,392,393,394, in particular a plurality of windings 391,392,393,394 consisting of conductive coils arranged on planes tangent to respective cylindrical surfaces 359 coaxial to stator 350. With such an arrangement, a rotation of rotor 351 causes reference pole 6N of actuation magnet 366 to face each manoeuvre electromagnets 391-394.

With such an arrangement, stabilization magnets 381,382 identify two positions of stable equilibrium for rotor 351 with respect to stator 350, where actuation pole 6N of actuation magnet 366 faces stabilization pole 8S of stabilization magnet 381 and of stabilization magnet 382, respectively.

Actuation magnet 366, is connected to valve unit 20 through rotor 351. In this way, when reference pole 6N of actuation magnet 366 is facing the first or second stabilization magnet 381,382, valve unit 20 is respectively in release configuration R and in block configuration B, as shown, or vice-versa. To this purpose, container 10 also encloses an actuation cylinder 330 rotatably arranged about its axis 19 and connected to second end portion 23 of torsionally compliant tubular body 20, so that a rotation of actuation cylinder 330 about its axis 19 causes a torsional deformation of torsionally compliant tubular body 20. End ring portion 352 of rotor 351 is constrained to actuation cylinder 330.

Artificial sphincter 301 also comprises a control unit 390 configured to selectively and consecutively supply a manoeuvre electric current to manoeuvre electromagnets 391-394, through an electric connection means 395, said current having an intensity selected so that each of them creates a magnetic field capable of causing rotor 351 to perform consecutive rotations and to bring reference pole 6N of actuation magnet 366 to consecutively face manoeuvre electromagnets 391,392,393,394, in this order or in the opposite order.

Still with reference to FIGS. 33A,33B, in order to fix control unit 390 to container 10, the former can have outwards radially protruding lock teeth 396 at an own end, said teeth configured to engage with lock channels 13 provided at end 10" of container 10.

The operation of artificial sphincter 100,120 will now be described with reference to FIGS. 37-39, showing partial section side views thereof with the container removed, in the block configuration, in an intermediate configuration and in a release configuration, and with reference to the corresponding cross sectional views of FIG. 34-36. In order to move endourethral sphincter 301 from the block configuration (FIGS. 34,37) to the release configuration (FIGS. 36,39), a remote control 397 is used to send an opening wireless signal 398 to control unit 390. This signal actuates a program means resident in control unit 390 and configured to operate in turn manoeuvre electromagnets 391,392,393, 394, in order to subsequently generate respective magnetic fields whose magnetic induction vectors, at the end portion of each winding, can cause rotor 351 to rotate from the open position of FIG. 34 to the closed position of FIG. 36.

Similarly, in order to bring endourethral sphincter 301 from the release configuration back to the block configuration, remote control 397 is used to send a closing wireless signal 399 to control unit 390. Control unit 390 is configured to subsequently actuate manoeuvre electromagnets 394,393, 392,391, upon receiving this signal, in this order, so as to subsequently generate magnetic fields whose magnetic induction vectors, at the end portion of each winding, can cause rotor 351 to rotate from the closed position of FIG. 36 to the open position of FIG. 34.

It falls within the scope of the present application also an artificial sphincter having a structure corresponding to any of those of the exemplary embodiments and of the respective modification thereof, as described above, in which stabilization magnets 80, 180, 381, 382 are respectively replaced by bodies of ferromagnetic material, suitable to create respective magnetic axes and magnetic poles when forced by an external manoeuvre magnet.

Fourth Exemplary Embodiment

With reference to FIGS. 46-50, an extraurethral artificial sphincter 401 is described according to a fourth exemplary embodiment comprising, like artificial sphincters 101 and 202, a container 10 with a cover 12 (FIGS. 47-50) and a valve unit 20 including a stopper 26 slidably arranged within container 10 to tighten a segment of urethra 4, and to allow it to dilate, i.e. to obtain a block configuration B and a release configuration R, respectively.

Artificial sphincter 401 comprises structural and functional elements that are present also in artificial sphincter 202, i.e. container 10, an actuation unit 460 comprising a fixed hollow cylindrical guide element 450, an actuation magnet 466, an actuation cylinder 430 and an integrally rotatable support 461 of actuation magnet 466, and also comprises slidable stopper 26 with pin 462 housed within a hole 463 and in both channels 456 and 436 of a guide element 450 and of an actuation cylinder 430. On the contrary, artificial sphincter 401 does not comprise any stabilization magnet, and has a lock ring 499 instead.

In order that both block condition B and release condition R are stable, i.e. they do not require the presence in situ of manoeuvre magnet 490 used for bringing sphincter 401 from block configuration B (FIG. 47) to release configuration R (FIG. 50) and vice-versa (FIG. 49), besides linear portion 451, channel 456 of guide element 450 has two circumferential end portions 452 and 453 arranged at a distance D, along longitudinal axis 19, that is at most equal to the height of channel 456.

Moreover, channels 436 and 456 are mutually positioned in such a way that, when pin 462 is in circumferential portion 452 (FIGS. 47 and 48) or in circumferential portion 453 (FIG. 50), slidable stopper 26 is in a more extended position and in a more retracted position, respectively, as shown in the figures, or vice-versa, with respect to guide element 450, and that valve unit 20 is in block configuration B and in release configuration R, respectively, as described with reference to artificial sphincter 202.

Figure 48:
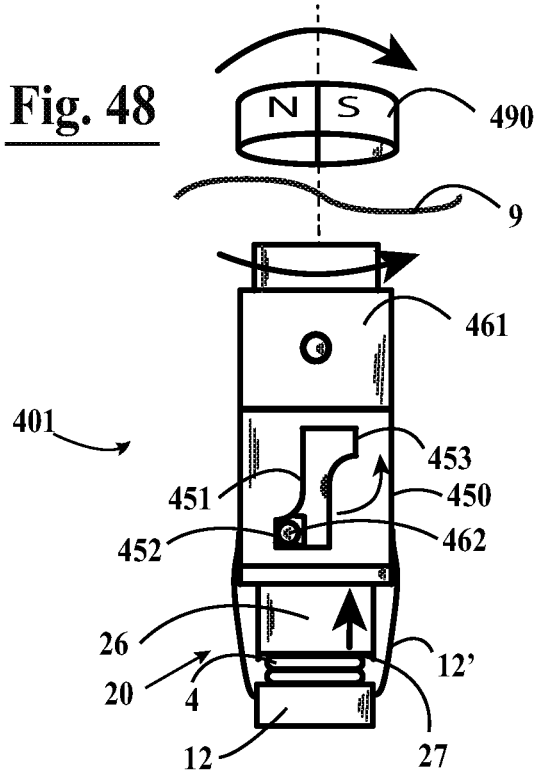
Figure 49:
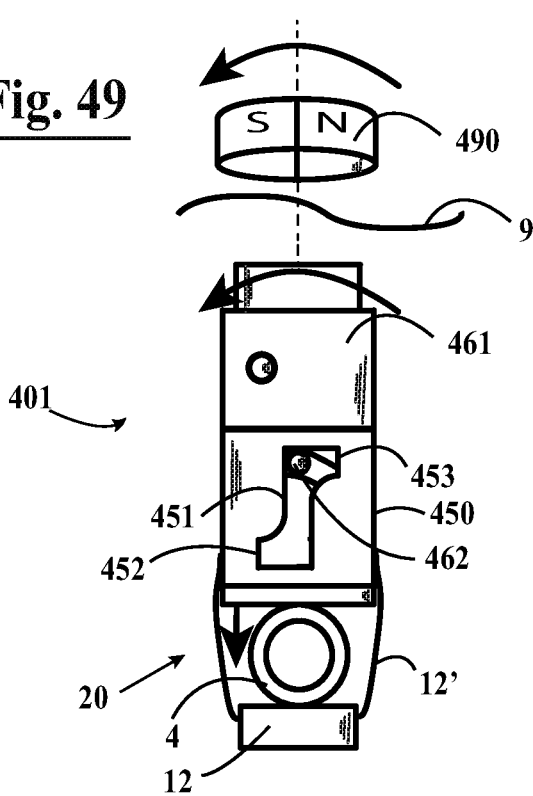
Figure 50:
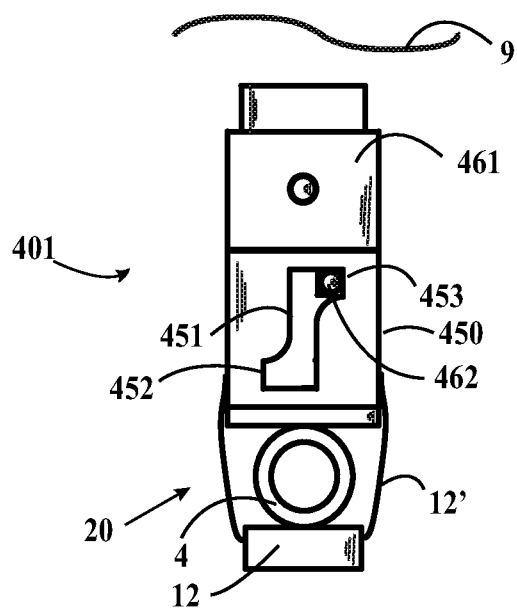

This way, when the pin engages with circumferential portions 452 or 453 of channel 456, corresponding to block configuration B and to release configuration R, respectively, any push action on stopper 26, for instance due to natural elasticity of urethra 4, or to such a cause as a cough and the like, cannot cause a translation movement of stopper 26. Block configuration B and release configuration R can be left by positioning a manoeuvre magnet 490 with the magnetic axis substantially perpendicular to axis 19 of container 10, and oriented so as to cause actuation magnet 466 to rotate, as shown in FIGS. 48 and 49.

The foregoing description of specific embodiments will so fully reveal the invention according to the conceptual point of view, so that others, by applying current knowledge, will be able to modify and/or adapt in various applications such specific embodiments without further research and without parting from the invention, and, accordingly, it is meant that such adaptations and modifications will have to be considered as equivalent to the embodiments exemplified. The means and the materials to put into practice the different functions described herein could have a different nature without, for this reason, departing from the field of the invention. It is to be understood that the phraseology or terminology that is employed herein is for the purpose of description and not of limitation.

The invention claimed is:
1. An artificial sphincter comprising:
   a container having a longitudinal axis, said container configured to be connected to a wall of a patient's urethra;
   a valve unit arranged within said container, and configured to reversibly move between:
   a release configuration, in which said valve unit is arranged to allow a passage of urine through said artificial sphincter, and
   a block configuration, in which said valve unit is arranged to prevent said passage of urine through said artificial sphincter;
   a stabilization magnet having poles arranged along a first magnetic axis, said stabilization magnet arranged integral to said container with said first magnetic axis parallel to said longitudinal axis,
   an actuation magnet having poles arranged along a second magnetic axis, parallel to said longitudinal axis, wherein said actuation magnet:
   is slidably arranged within said container, in order to change its own distance from said stabilization magnet along said longitudinal axis and to responsively change the magnetic force between said actuation magnet and said stabilization magnet; and
   is connected to said valve unit in such a way that a translation movement of said actuation magnet under the effect of an external maneuver magnetic field, causes said valve unit to move between said release configuration and said block configuration,
   a resilient element having a first end integral to said container and a second end, opposite to said first end, connected to said actuation magnet, so that said actuation magnet receives a resilient force responsive to said distance along said container, wherein said resilient element, said actuation magnet and said stabilization magnet are arranged in such a way that:
  said magnetic force has a direction opposite to said resilient force; said
  magnetic force has an intensity higher than said resilient force when said actuation magnet is distanced less than a predetermined equilibrium distance (d*) from said stabilization magnet; and
  said magnetic force has an intensity lower than said resilient force when said actuation magnet is distanced more than said equilibrium distance from said stabilization magnet,
  such that, if said actuation magnet is distanced less/more than said equilibrium distance, respectively, with respect to said stabilization magnet, said actuation magnet maintains/brings said valve unit in said release/block configuration.

2. An artificial sphincter according to claim 1, wherein:
said container is configured to be connected within said urethra;
said valve unit comprises a slidable stopper slidably arranged within said container, said actuation magnet integral to said slidable stopper,
said slidable stopper has a stopper abutment element and said artificial sphincter comprises a sealing housing arranged to fluid-tightly engage with said stopper abutment element when said actuation magnet is in an advanced position along with said slidable stopper, obtaining said block configuration,
said sealing housing is selected from the group consisting of:
  a sealing element of an inner wall of said container, configured to directly engage with said stopper abutment element;
  a resilient shell portion of a valve element having at least one through notch, wherein said resilient shell portion is configured to move:
    from a closed configuration, in which said resilient shell portion has a convex shape opposite to said slidable stopper and forms a diaphragm, such that a urine pressure on said resilient shell portion maintains said through notch closed;
    to an open configuration, in which said resilient shell portion has a concave shape opposite to said convex shape, wherein said through notch is deformed and open, and is configured to allow said passage of urine,
  in said convex shape, said resilient shell portion is configured to bear said urine pressure up to a pressure limit, above which said resilient shell portion collapses into said concave shape, so as to allow said passage of urine through said through notch, and
  said stopper abutment element is configured to prevent said resilient shell portion from moving from said closed configuration to said open configuration when said stopper abutment element engages with said resilient shell portion.

3. An artificial sphincter according to claim 1, wherein:
said container comprises a main body and a cover at an end portion thereof, and is configured to be crossed by a segment of said urethra at said end portion;
said valve unit comprises a slidable stopper slidably arranged within said container, said actuation magnet integral to said slidable stopper,
such that, when said actuation magnet is in said block configuration, a stopper abutment element of said slidable stopper engages with said cover, so as to press and close said segment of urethra, in order to prevent said passage of urine through said urethra, whereas, when said actuation magnet is in said released configuration, said stopper abutment element is at a predetermined distance from said cover, in order to allow said segment of urethra to reach an open configuration, and to allow said passage of urine.

4. An artificial sphincter according to claim 1, wherein:
said longitudinal axis of said container is a first longitudinal axis,
said container is configured to be connected within said urethra;
said valve unit comprises a torsionally compliant tubular body with an own second longitudinal axis parallel to said longitudinal axis, and comprising:
  first and a second end portions, said first end portion integral to said container;
  a central portion torsionally compliant about said second longitudinal axis, wherein an opening/closing torsional deformation of said central portion brings said torsionally compliant tubular body:
    from said release configuration, in which said torsionally compliant central portion defines a passageway in said torsionally compliant tubular body along said second longitudinal axis, and
    to said block configuration, in which inner walls of said torsionally compliant central portion are in contact with one another so as to completely block said passageway in at least one part of said central portion or
    vice-versa,
said artificial sphincter also comprises:
  an actuation unit comprising:
    said actuation magnet;
    a hollow cylindrical guide element arranged within and integral to said container, wherein said guide element has a first channel
    having a helical portion;
    a rotatable actuation cylinder, rotatably arranged within said container about said longitudinal axis, and having:
      an end part integral to said second end portion of said torsionally compliant tubular body;
      a channelled part having a linear second channel, wherein said channelled part telescopically engages with said guide element at said first channel;
      at least one outer radial protrusion integral to said actuation magnet and engaging with both said first and second channels;
  such that said translation movement of said actuation magnet brings said at least one outer radial protrusion from a first position to a second position along said helical portion of said first channel, thus causing said opening/closing torsional deformation and causing said valve unit to move from said release configuration to said block configuration or vice-versa.

5. An artificial sphincter according to claim 4, wherein said first channel comprises a linear longitudinal end portion adjacent to one position, among the first and the second positions, positions, that correspond to said block configuration.

6. An artificial sphincter according to claim 1, further comprising:

a maneuver electromagnet arranged to create the maneuver magnetic field having a maneuver magnetic axis substantially parallel to said longitudinal axis; and a control unit configured to supply an electric current to said maneuver electromagnet, said electric current having:

a first or a second direction, selected in such a way that said maneuver magnetic axis has the same orientation as or the opposite orientation with respect to said second magnetic axis, so that said actuation magnet receives a maneuver magnetic force having the same direction or the opposite direction, respectively, with respect to said magnetic force and, accordingly, the opposite direction or the same direction, respectively, with respect to said resilient force; and an intensity selected in such a way that said maneuver magnetic force having said same or opposite direction causes said actuation magnet to carry out said translation movement so as to bring said actuation magnet from said retracted position to said advanced position, respectively, or vice-versa, causing said valve unit to move from said release configuration to said block configuration, respectively, or vice-versa.

7. An artificial sphincter according to claim 6, wherein said maneuver electromagnet comprises a winding of coils of an electrically conductive material arranged on respective planes substantially perpendicular to said longitudinal axis.

8. An artificial sphincter according to claim 1, wherein said resilient element comprises a cylindrical helical spring.

* * * * *